US012781284B2

(12) United States Patent
Tokarz et al.

(10) Patent No.: US 12,781,284 B2
(45) Date of Patent: Nov. 3, 2026

(54) SEROLOGICAL ASSAY FOR DETECTION OF EXPOSURE TO AND INFECTION BY TICK-BORNE PATHOGENS

(71) Applicant: THE TRUSTEES OF COLUMBIA UNIVERSITY IN THE CITY OF NEW YORK, New York, NY (US)

(72) Inventors: Rafal Tokarz, Queens Village, NY (US); Walter Ian Lipkin, New York, NY (US); Nischay Mishra, New York, NY (US); Thomas Briese, White Plains, NY (US); Adrian Caciula, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1408 days.

(21) Appl. No.: 16/828,483

(22) Filed: Mar. 24, 2020

(65) Prior Publication Data

US 2020/0255889 A1 Aug. 13, 2020

Related U.S. Application Data

(63) Continuation-in-part of application No. PCT/US2018/052625, filed on Sep. 25, 2018.

(60) Provisional application No. 62/562,634, filed on Sep. 25, 2017, provisional application No. 62/848,701, filed on May 16, 2019.

(51) Int. Cl.

| | |
|---|---|
| ***C12Q 1/689*** | (2018.01) |
| ***C07K 7/08*** | (2006.01) |
| ***C12Q 1/6883*** | (2018.01) |
| ***C40B 40/10*** | (2006.01) |

(52) U.S. Cl.

CPC ................ *C12Q 1/689* (2013.01); *C07K 7/08* (2013.01); *C12Q 1/6883* (2013.01); *C12Q 2600/112* (2013.01); *C12Q 2600/124* (2013.01); *C12Q 2600/156* (2013.01); *G01N 2333/195* (2013.01); *G01N 2800/26* (2013.01)

(58) Field of Classification Search

None

See application file for complete search history.

(56) References Cited

U.S. PATENT DOCUMENTS

| | | | | |
|---|---|---|---|---|
| 6,905,816 | B2 | 6/2005 | Jacobs et al. | |
| 10,393,741 | B2 * | 8/2019 | Rikihisa | C07K 14/29 |
| 2002/0169136 | A1 * | 11/2002 | Reed | C07K 14/44 514/44 R |
| 2008/0248497 | A1 * | 10/2008 | Beall | G01N 33/56911 530/300 |
| 2009/0162875 | A1 * | 6/2009 | Dattwyler | G01N 33/569 530/328 |
| 2013/0177978 | A1 | 7/2013 | Mcbride et al. | |
| 2013/0244258 | A1 * | 9/2013 | Erwin, III | G01N 33/56905 435/7.92 |
| 2015/0119276 | A1 | 4/2015 | Mcbride et al. | |
| 2016/0289746 | A1 | 10/2016 | Parveen et al. | |
| 2017/0014820 | A1 | 1/2017 | Lee et al. | |

FOREIGN PATENT DOCUMENTS

| | | | | |
|---|---|---|---|---|
| EP | 1589109 | A2 * | 10/2005 | A61K 39/44 |
| WO | WO 02/057794 | | 7/2002 | |
| WO | WO 2013/116668 | | 8/2013 | |
| WO | WO/2016/118766 | | 7/2016 | |

OTHER PUBLICATIONS

Yonekita et al. J Microbiol Meth 93: 251-256, 2013 (Year: 2013).*

Singh et al. Food Chem 170: 470-483, 2015 (Year: 2015).*

Koczula et al (Essays Biochem 60: 111-120, 2016).*

Chan et al., "Sensitive multiplex PCR assay to differentiate Lyme spirochetes and emerging pathogens Anaplasma phagocytophilum and Babesia microti", BMC Microbiol. Dec. 20, 2013; 13: 295.

Lahey et al., "Development of a Multiantigen Panel for Improved Detection of Borrelia burgdorferi Infection in Early Lyme Disease", vol. 53 / Issue 12, pp. 3834-3841, Dec. 2015.

Lipkin, "The changing face of pathogen discovery and surveillance", vol. 11, pp. 133-141, Feb. 2013.

Qurollo et al. "Improved molecular detection of Babesia infections in animals using a novel quantitative real-time PCR diagnostic assay targeting mitochondrial DNA", vol. 10 / Issue 1, pp. 128, Mar. 2017.

Tagliabue et al., "A label-free immunoassay for Flavivirus detection by the Reflective Phantom Interface technology", vol. 492, Issue 4, Oct. 28, 2017, pp. 558-564.

Ghodbane et al., "Development and Validation of a Microfluidic Immunoassay Capable of Multiplexing Parallel Samples in Microliter Volumes", vol. 15 / Issue 15, pp. 3211-3221, Aug. 2015.

Adams, et al. Summary of Notifiable Infectious Diseases and Conditions—United States, Oct. 23, 2013. Morb. Mortal Wkly. Rep. 2015 62:1-122.

Adrion, et al. Health care costs, utilization and patterns of care following Lyme disease. PLoS One 2015 10:e0116767. Received Jul. 23, 2014.

Aguero-Rosenfeld, et al. Diagnosis of Lyme Borreliosis. Clin. Microbiol. Rev. Jul. 2005 18:484-509.

Aliota, et al. The prevalence of zoonotic tick-borne pathogens in Ixodes scapularis collected in the Hudson Valley, New York State. Vector Borne Zoonotic Dis. Apr. 2014 14:245-50.

(Continued)

*Primary Examiner* — Kimberly Ballard

*Assistant Examiner* — Aditi Dutt

(74) *Attorney, Agent, or Firm* — Amster, Rothstein & Ebenstein LLP

(57) ABSTRACT

The current invention provides compositions, methods, and kits for detecting the exposure to and infection by certain agent or pathogens. Specifically, the current invention allows for the rapid differential serological detection of exposure to, and infection by tick-borne agents or pathogens using specific antigenic peptides.

18 Claims, 7 Drawing Sheets

Specification includes a Sequence Listing.

(56) References Cited

OTHER PUBLICATIONS

Anderson et al. "Development and evaluation of a Luminex multiplex serology assay to detect antibodies to bovine herpes virus 1, parainluenza 3 virus, bovine viral diarrhoea virus, and bovine respiratory syncytial virus, with comparison to existing ELISA detection methods", J. Immunol. Methods 2011 366:79-88. Revied Oct. 8, 2010.
Ang, et al. Large differences between test strategies for the detection of anti-Borrelia antibodies are revealed by comparing eight ELISAs and five immunoblots. Eur. J. Clin. Microbiol. Infect. Dis. 2011 30:1027-32. Received Jul. 21, 2010.
Bacon, et al. Serodiagnosis of Lyme disease by kinetic enzyme-linked Immunosorbent assay using recombinant VlsE1 or peptide antigens of Borrelia burgdorferi compared with 2-tiered testing using whole-cell lysates. J. Infect. Dis. Apr. 15, 2003 187:1187-99.
Barbour, Multiple and Diverse vsp and vlp Sequences in Borrelia miyamotoi, a Hard Tick-Borne Zoonotic Pathogen. PLoS One 2016 11:e0146283. Received Nov. 16, 2015.
Barbour, et al. A genome-wide proteome array reveals a limited set of immunogens in natural infections of humans and white-footed mice with Borrelia burgdorferi. Infect. Immun. Jan. 14, 2008 76:3374-89.
Biggs, et al. Diagnosis and Management of Tickborne Rickettsial Diseases: Rocky Mountain Spotted Fever and Other Spotted Fever Group Rickettsioses, Ehrlichioses, and Anaplasmosis—United States. MMWR Recomm. Rep. May 13, 2016 65:1-44.
Buus, et al. High-resolution mapping of linear antibody epitopes using ultrahigh-density peptide microarrays. Mol. Cell. Proteomics May 29, 2012 11:1790-800.
Centers for Disease Control, Prevention. Recommendations for test performance and interpretation from the Second National Conference on Serologic Diagnosis of Lyme Disease. Morb. Mortal. Wkly. Rep. Aug. 11, 1995 44:590-1.
Connally, et al. Testing practices and volume of non-Lyme tickborne diseases in the United States. Tick Borne Dis. Feb. 2016 7:193-8.
Cornillot, et al. A targeted immunomic approach identifies diagnostic antigens in the human pathogen Babesia microti. Transfusion Aug. 2016.
Fallon, et al. A comparison of Lyme disease serologic test results from four laboratories in patients with persistent symptoms after antibiotic treatment. Clin. Infect. Dis. Dec. 15, 2014 59:1705-10.
Gong, et al. Identification of novel surface-exposed proteins of Rickettsia rickettsii by affinity purification and proteomics. PLoS One Jun. 2014 9:e100253.
Hinckley, et al. Lyme disease testing by large commercial laboratories in the United States. Clin. Infect. Dis. Sep. 1, 2014 59:676-81.
Houghton, et al. Identification of Babesia microti-specific immunodominant epitopes and development of a peptide EIA for detection of antibodies in serum. Transfusion Nov. 2002 42:1488-96.
Jahfari, et al. High seroprevalence of Borrelia miyamotoi antibodies in forestry workers and individuals suspected of human granulocytic anaplasmosis in the Netherlands. New Microbes New Infect. Apr. 29, 2014 2:144-9.
Khatchikian, et al. Recent and rapid population growth and range expansion of the Lyme disease tick vector, Ixodes scapularis, in North America. Evolution 2015 69:1678-89. Received Apr. 30, 2014.
Krause, et al. Borrelia miyamotoi sensu lato seroreactivity and seroprevalence in the northeastern United States. Emerg Infect. Dis. Jul. 2014 20:1183-90.
Kosoy, et al. Novel thogotovirus associated with febrile illness and death, United States, 2014. Emerg Infect Dis May 2015;21:760-4.
Krbkova, et al. Assessment of antibodies against surface and outer membrane proteins of Anaplasma phagocytophilum in Lyme borreliosis and tick-borne encephalitis paediatric patients. Epidemiol. Infect. Sep. 10, 2016 144:2597-604.
Kugeler, et al. Geographic Distribution and Expansion of Human Lyme Disease, United States. Emerg. Infect. Dis. Sep. 10, Aug. 2015 21:1455-7.
Liang, et al. Sensitive and specific serodiagnosis of Lyme disease by enzyme-linked immunosorbent assay with a peptide based on an immunodominant conserved region of Borrelia burgdorferi vlsE. J. Clin. Microbiol. Dec. 1999 37:3990-6.
Lodes, et al. Serological expression cloning of novel immunoreactive antigens of Babesia microti. Infect, Immun, May 2000 68:2783-90.
Masatani, et al. Identification, cloning and characterization of BmP41, a common antigenic protein of Babesia microti. J. Vet, Med, Sci, 2013 75:967-70. Received Dec. 9, 2012.
Masters, et al. STARI, or Masters disease: Lone Star tick-vectored Lyme-like illness. Infect. Dis. Clin. North Am. Jun. 2008 22:361-76.
Molins, et al. Collection and characterization of samples for establishment of a serum repository for Lyme disease diagnostic test development and evaluation. J. Clin. Microbiol. Oct. 2014 52:3755-62.
Nelder, et al. Human pathogens associated with the blacklegged tick Ixodes scapularis: a systematic review. Parasit. Vectors Feb. 24, 2016 9:265.
Nelson, et al. Incidence of Clinician-Diagnosed Lyme Disease, United States, 2005-2010. Emerging Infect. Dis. Sep. 21, 2015:1625-31.
Pastula, et al. Notes from the field: Heartland virus disease—United States, 2012-2013. Morb. Mortal. Wkly. Rep. Mar. 28, 2014 63:270-1.
Piantadosi, et al. Emerging Cases of Powassan Virus Encephalitis in New England: Clinical Presentation, Imaging, and Review of the Literature. Clin. Infect. Dis. Mar. 15, 2016 62:707-13.
Porwancher, et al. Multiplex immunoassay for Lyme disease using VlsE1-IgG and pepC10-IgM antibodies: improving test performance through bioinformatics. Clin. Vaccine Immunol. May 2011 18:851-9.
Robinson, et al. "Autoantigen microarrays for multiplex characterization of autoantibody responses", Nat. Med. Mar. 2002 8:295-301.
Schwan, et al. GlpQ: an antigen for serological discrimination between relapsing fever and Lyme borreliosis. J. Clin. Microbiol. Oct. 1996 34:2483-92.
Seriburi, et al. High frequency of false positive IgM immunoblots for Borrelia burgdorferi in clinical practice. Clin. Microbiol. Infect. 2012 18:1236-40. Sep. 16, 2011.
Signorino et al. Identification of OppA2 linear epitopes as serodiagnostic markers for Lyme disease. Clin Vaccine Immunol May 2014;21:704-11.
Stromdahl, et al. Beyond Lyme: aetiology of tick-borne human diseases with emphasis on the south-eastern United States. Zoonoses Public Health 2012 59 Suppl 2:48-64. Received Oct. 7, 2011.
Theel The Past, Present, and (Possible) Future of Serologic Testing for Lyme Disease. J. Clin. Microbiol. May 2016;54:1191-6.
Tokarz, et al. Detection of Anaplasma phagocytophilum, Babesia microti, Borrelia burgdorferi, Borrelia miyamotoi, and Powassan Virus in Ticks by a Multiplex Real-Time Reverse Transcription-PCR Assay. mSphere Mar./Apr. 2, 2017.
Tokarz, et al. Genome characterization of Long Island tick rhabdovirus, a new virus identified in Amblyomma americanum ticks. Virol. J. Jan. 15, 2014 11:26.
Tokarz, et al. Assessment of polymicrobial infections in ticks in New York state. Vector Borne Zoonotic Dis. Apr. 2010 10:217-21.
Tokarz, et al. Combined effects of blood and temperature shift on Borrelia burgdorferi gene expression as determined by whole genome DNA array. Infect. Immun. Sep. 2004 72:5419-32.
Vigil, et al. "Defining the humoral immune response to infectious agents using high-density protein microarrays", Future Microbiol. Feb. 2010 5:241-51.
Wagemakers et al. Variable Major Proteins as Targets for Specific Antibodies against Borrelia miyamotoi. J. Immunol. May 15, 2016 196:4185-95.
Wormser, et al. Single-tier testing with the C6 peptide ELISA kit compared with two-tier testing for Lyme disease. Diagn. Microbio.l Infect. Dis. November 12013 75:9-15.

(56) References Cited

OTHER PUBLICATIONS

Xu, et al. Profiling the humoral immune response to Borrelia burgdorferi infection with protein microarrays. Microb. Pathog. Apr. 24, 2008 45:403-7.
Yu, et al. Comparison of Ehrlichia chaffeensis recombinant proteins for serologic diagnosis of human monocytotropic ehrlichiosis. J. Clin. Microbiol. Aug. 1999 37:2568-75.
Doyle C Kuyler et al: "Differentially expressed and secreted major immunoreactive protein orthologs of Ehrlichia canis and E-chaffeensis elicit early antibody responses to Epitopes on glycosylated tandem repeats", Infection and Immunity, American Society for Microbiology, US, vol. 74, No. 1, Jan. 1, 2006 (Jan. 1, 2006), pp. 711-720, XP002406352, ISSN: 0019-9567, DOI: 10.1128/IAI.74.1.711-720.2006.
Tian Luo et al: "Abstract", Clinical and Vaccine Immunology, vol. 17, No. 1, Dec. 2, 2009 (Dec. 2, 2009), pp. 87-97, XP55732892, ISSN: 1556-6811, DOI: 10.1128/CVI.00331-09.
Jordan V Price et al: "On silica peptide microarrays for high-resolution mapping of antibody epitopes and diverse protein-protein interactions", Nature Medicine, vol. 18, No. 9, Aug. 19, 2012 (Aug. 19, 2012), pp. 1434-1440, XP055586188, New York ISSN: 1078-8956, DOI: 10.1038/nm.2913.

* cited by examiner

| | PEPTIDES |
|---|---|
| 1 | EMKKDDQIAAAI (SEQ ID NO: 50) |
| 2 | MKKDDQIAAAIA (SEQ ID NO: 44) |
| 3 | KKDDQIAAAIAL (SEQ ID NO: 45) |
| 4 | KDDQIAAAIALR (SEQ ID NO: 46) |
| 5 | DDQIAAAIALRG (SEQ ID NO: 47) |
| 6 | DQIAAAIALRGM (SEQ ID NO: 48) |
| 7 | QIAAAIALRGMA (SEQ ID NO: 49) |
| 8 | IAAAIALRGMAK (SEQ ID NO: 51) |
| 9 | AAAIALRGMAKD (SEQ ID NO: 52) |

SEROLOGICAL ASSAY FOR DETECTION OF EXPOSURE TO AND INFECTION BY TICK-BORNE PATHOGENS

CROSS REFERENCE TO RELATED APPLICATION

The present application claims priority and is a continuation-in-part to International Patent Application Serial No. PCT/US2018/05625 filed Sep. 25, 2018 which claims priority to U.S. Provisional Patent Application Ser. No. 62/562,634 filed Sep. 25, 2017, and this application also claims priority to U.S. Patent Application Ser. No. 62/848,701 filed May 16, 2019, all of which are hereby incorporated by reference in their entirety.

STATEMENT OF GOVERNMENT SUPPORT

This invention was made with government support under AI109761 awarded by the National Institutes of Health. As such, the United States government has certain rights in this invention.

FIELD OF THE INVENTION

This invention relates to the field of detection of exposure to tick-borne pathogens using high throughput serology and novel peptide antigens.

BACKGROUND OF THE INVENTION

Tick-borne diseases (TBD) are the most common vector-borne diseases in the United States (Adams et al. 2013). As of 2017, nineteen bacterial, protozoan and viral agents have been implicated in TBDs. *Borrelia Burgdorferi*, the causative agent for Lyme disease alone accounts for an estimated 300,000 cases of tick-borne disease and the total annual direct medical costs of Lyme disease are estimated to range between $700 million and $1.3 billion (Nelson et al. 2015; Hinkley et al. 2014; Adrion et al. 2015). Other agents implicated in TBD throughout the United States include *Borrelia miyamotoi, Babesia microti, Anaplasma phagocytophilum, Ehlichia chaffeensis, Rickettsia rickettsia*, Colorado tick fever virus, Heartland virus, and Powassan virus (POWV) (Nelder et al. 2016; Stromdahl et al. 2012). Additional pathogens continue to be discovered.

Approximately three million specimens are tested for tick-borne infections annually with serology being the mainstay of diagnosis. When a patient presents with clinical symptoms indicative of TBD in an endemic area, clinicians tend to employ serological tests for *Borrelia Burgdorferi*, as molecular assays have limited utility because tick-borne pathogens in blood are transient and present in only low concentrations (Connally et al. 2016; Theel 2016; CDC 1995).

For Lyme disease, the recommended two-tier serologic testing has high specificity and sensitivity for disseminated disease but its utility in the early acute disease phase is limited (Aguero-Rosenfeld et al. 2005; Molins et al. 2014). Among the key reasons for this deficiency include the non-specificity of IgM, low or undetectable IgG, and differential expression of *B. burgdorferi* antigens. *B. burgdorferi* undergoes substantial remodeling of its outer surface throughout infection (Tokarz et al. 2004). As a result, the expression of some commonly used diagnostic antigens during the early stages of infection are not sufficient to trigger an effective antigen-specific immune response (Wormser et al. 2013). This testing only accurately identifies less than 40% of patients with early disease and can result in up to 28% of IgM western blots yielding false positive results (Aguero-Rosenfeld et al. 2005; Seriburi et al. 2012). This method is also laborious and costly, and the results are subject to interpretation (Fallon et al. 2014; Ang et al. 2011). Assays are strain-dependent and for some agents can only be performed in specialized laboratories (Theel 2016).

Indirect immunofluorescent assay (IFA) is recommended for diagnosis of tick-borne infections with *Babesia, Anaplasma, Ehrlichia* and *Rickettsia*. The accuracy of IFAs can vary widely among testing laboratories primarily due to the lack of standardized antigenic targets, cross reactivity, and subjective establishment of positivity thresholds (Biggs et al. 2016). For other tick-borne agents, specific serologic tests are not yet available, or in the case of Powassan virus or Heartland virus, are only performed in specialized laboratories (Pastula et al. 2014; Piantadosi et al. 2016). An additional challenge is the lack of assays that simultaneously test for exposure to the full spectrum of tick-borne pathogens. This is an important limitation in TBD diagnosis in light of surveillance studies that indicate ticks frequently carry more than one human pathogen (Aliota et al. 2014; Tokarz et al. 2010; Tokarz et al. 2017).

The reported incidence of TBDs has risen continuously over the past three decades in association with geographic expansion of tick populations and the discovery of a wide range of novel tick-borne pathogens (Khatchikian et al. 2015; Kugeler et al. 2015). Nonetheless, the true incidence of TBDs is likely greatly underestimated, as patients with presumed TBDs are rarely tested for the full range of tick-borne pathogens, and only a fraction of positive cases are properly reported (White et al. 2016). New diagnostic assays that can detect infections with the full range of tick-borne pathogens are urgently needed, and in particular there is a need for a sensitive, specific, and inexpensive high throughput serological assay for the detection of tick-borne pathogens including, but not limited to, *Borrelia burgdorferi, Borrelia miyamotoi, Babesia microti, Anaplasma phagocytophilum, Ehlichia chaffeensis, Rickettsia rickettsii*, Heartland virus, Powassan virus, and, as well as to discriminate between various stages of Lyme disease in order to expand the window of accurate diagnosis. These aims will enable new strategies for diagnosing and investigating the epidemiology and pathogenesis of acute TBD and persistent conditions such as Post-treatment Lyme Disease Syndrome (PTLDS).

SUMMARY OF THE INVENTION

The current invention addresses the current limitations in differential diagnosis of TBD through the development of a programmable, multiplex, high-resolution peptide array platform that can detect antibodies to all key pathogens currently implicated in TBD and can be expanded as new pathogens are encountered.

The current invention provides compositions, methods, and kits for detecting the exposure to and infection by tick-borne pathogens. Specifically, the current invention allows for the rapid simultaneous and differential serological detection of exposure to, and infection by tick-borne pathogens. In particular, the current invention allows for the rapid simultaneous serological detection of exposure to, and infection by *Borrelia burgdorferi, Borrelia miyamotoi, Babesia microti, Anaplasma phagocytophilum, Ehlichia chaffeensis, Rickettsia rickettsii*, Heartland virus, and Powassan virus.

The compositions, methods and kits for detection of exposure to, and infection by *Borrelia burgdorferi*, as well as *Borrelia miyamotoi, Babesia microti, Anaplasma phagocytophilum, Ehlichia chaffeensis, Rickettsia rickettsii*, Heartland virus, and Powassan virus comprise specific peptides, isolated and non-isolated, which are strongly reactive with, and specific for each pathogen, i.e., reactive and specific epitopes of antibodies to each pathogen.

Thus, one embodiment of the present invention are the peptides listed in Table 1, which are reactive with, and specific for antibodies to the tick-borne pathogens (SEQ ID NOs: 1-19 and 29-43 and 60-97) as well as fragments and variants thereof (e.g., SEQ ID NOs: 98-110).

A further embodiment of the present invention are collections or sets of peptides which are strongly reactive with, and specific for each pathogen, i.e., reactive and specific epitopes of antibodies to each pathogen, comprising amino acid sequences shifted one residue across the peptide comprising the amino acid sequence of any one of SEQ ID NOs: 1-19 and 29-43 and 60-97 as well as fragments and variants thereof (e.g., SEQ ID NOs: 98-110).

One embodiment of the current invention is a collection or set of peptides which are strongly reactive with, and specific for all of the following tick-borne pathogens, *Borrelia burgdorferi, Borrelia miyamotoi, Babesia microti, Anaplasma phagocytophilum, Ehlichia chaffeensis, Rickettsia rickettsii, Borrelia miyamotoi*, Heartland virus, and Powassan virus, comprising amino acid sequences shifted one residue across all of the peptides comprising the amino acid sequences of SEQ ID NOs: 1-19 and 29-43 and 60-97.

A further embodiment of the present invention are peptides listed in Table 6 which are strongly reactive with, and specific for IgG epitopes of *Borrelia burgdorferi*, as well as collections or sets of peptides comprising amino acid sequences shifted one residue across the peptide comprising the amino acid sequence of any one of SEQ ID NOs: 1, 2, 4, 7, 8, and 20-28. A further embodiment of the present invention is a collection or set of peptides comprising amino acid sequences shifted one residue across all of the peptides comprising the amino acid sequences of SEQ ID NOs: 1, 2, 4, 7, 8, and 20-28. These peptides are particularly useful for diagnosis of acute neuroborreliosis.

These various collections or sets of peptides can comprise peptides that are 6 amino acids in length, 7 amino acids in length, 8 amino acids in length, 9 amino acids in length, 10 amino acids in length, 11 amino acids in length, and up to 12 amino acids in length.

The collection or set of peptides used in the present invention can range from 2 peptides to a number in the thousands to tens of thousands to hundreds of thousands. In the some of the Examples over 169,000 unique peptide sequences were used.

In another aspect, the invention provides compositions comprising two or more peptides of the invention.

In another aspect, the invention provides nucleic acids comprising a sequence encoding a peptide of the invention. In addition, the invention provides vectors comprising such nucleic acids, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

A further embodiment of the present invention is a peptide microarray comprising peptides, which are reactive with, and specific for antibodies of the tick-borne pathogens. In some embodiments, the peptide microarray comprises: at least one peptide comprising any one of the amino acid sequences in SEQ ID NOs: 1-19 and 29-43 and 60-97 as well as fragments and variants thereof (e.g., SEQ ID NOs: 98-110); or at least one collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof. In a further embodiment, the peptide microarray comprises a collection or set of peptides which are strongly reactive with, and specific for all of the following tick-borne pathogens, *Borrelia burgdorferi, Borrelia miyamotoi, Babesia microti, Anaplasma phagocytophilum, Ehlichia chaffeensis, Rickettsia rickettsii*, Heartland virus, and Powassan virus, comprising amino acid sequences shifted one residue across all of the peptides comprising the amino acid sequences of SEQ ID NOs: 1-19 and 29-43 and 60-97.

In a further embodiment, the peptide microarray comprises: at least one peptide listed in Table 6 which is strongly reactive with, and specific for IgG epitopes of *Borrelia burgdorferi*; or at least one collection or set of peptides comprising amino acid sequences shifted one residue across the peptide comprising the amino acid sequence of any one of SEQ ID NOs: 1, 2, 4, 7, 8, and 20-28; or combinations thereof. In a further embodiment, the peptide array comprises a collection or set of peptides comprising amino acid sequences shifted one residue across all of the peptides comprising the amino acid sequences of SEQ ID NOs: 1, 2, 4, 7, 8, and 20-28.

In another aspect, the invention provides devices. In certain embodiments, the devices are useful for performing an immunoassay. For example, in certain embodiments, the device is a lateral flow immunoassay device. In other embodiments, the device is an analytical or centrifugal rotor. In other embodiments, the device is a tube or a well, e.g., in a plate suitable for an ELISA assay or a microarray. In still other embodiments, the device is an electrochemical, optical, or opto-electronic sensor.

In certain embodiments, the device comprises at least one peptide of the invention. In other embodiments, the device comprises a collection or set of the peptides of the invention as described herein. In certain embodiments, the peptides are attached to or immobilized upon the device.

A further embodiment of the present invention is a method for the serological detection of exposure to and/or infection by one or more of the tick-borne pathogens, comprising the use of a peptide or peptides which are reactive with, and specific for the antibodies to the tick-borne pathogens comprising: at least one peptide comprising any one of the amino acid sequences in SEQ ID NOs: 1-19 and 29-43 and 60-97 as well as fragments and variants thereof (e.g., SEQ ID NOs: 98-110); or at least one collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof.

A further embodiment of the present invention is a method for the simultaneous serological detection of exposure to and/or infection by all of the following tick-borne pathogens, *Borrelia burgdorferi, Borrelia miyamotoi, Babesia microti, Anaplasma phagocytophilum, Ehlichia chaffeensis, Rickettsia rickettsii*, Heartland virus, and Powassan virus, comprising the use of a set or collection of peptides, comprising amino acid sequences shifted one residue across all of the peptides comprising the amino acid sequences of SEQ ID NOs: 1-19 and 29-43 and 60-97.

A further embodiment of the present invention is a method for the serological detection of acute neuroborreliosis, comprising the use of a peptide or peptides which are reactive with, and specific for the antibodies to the tick-borne pathogens comprising: at least one peptide comprising any one of the amino acid sequences in SEQ ID NOs: 1, 2, 4, 7, 8, and 20-28; or at least one collection or set of peptides comprising amino acid sequences shifted one residue across at least one peptide comprising any one of the amino acid sequences in SEQ ID NOs: 1, 2, 4, 7, 8, and 20-28; or combinations thereof.

A further embodiment of the present invention is a method for the serological detection of acute neuroborreliosis, comprising the use of a collection or set of peptides comprising amino acid sequences shifted one residue across all of the peptides comprising the amino acid sequences of SEQ ID NOs: 1, 2, 4, 7, 8, and 20-28.

A further embodiment of the present invention is a method for the serological detection of exposure to and/or infection by one or more of the tick-borne pathogens, comprising the use of peptide microarray comprising peptides which are reactive with, and specific for antibodies to the tick-borne pathogens comprising: at least one peptide comprising any one of the amino acid sequences in SEQ ID NOs: 1-19 and 29-43 and 60-97 as well as fragments and variants thereof (e.g., SEQ ID NOs: 98-110); or at least one collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof.

A further embodiment of the present invention is a method for the simultaneous serological detection of exposure to and/or infection by all of the following tick-borne pathogens, *Borrelia burgdorferi, Borrelia miyamotoi, Babesia microti, Anaplasma phagocytophilum, Ehlichia chaffeensis, Rickettsia rickettsii*, Heartland virus, and Powassan virus, comprising the use of peptide microarray comprising a set or collection of peptides, comprising amino acid sequences shifted one residue across all of the peptides comprising the amino acid sequences of SEQ ID NOs: 1-19 and 29-43 and 60-97.

A further embodiment of the present invention is a method for the serological detection of acute neuroborreliosis, comprising the use of peptide microarray comprising a peptide or peptides which are reactive with, and specific for the antibodies to the tick-borne pathogens comprising: at least one peptide comprising any one of the amino acid sequences in SEQ ID NOs: 1, 2, 4, 7, 8, and 20-28; or at least one collection or set of peptides comprising amino acid sequences shifted one residue across at least one peptide comprising any one of the amino acid sequences in SEQ ID NOs: 1, 2, 4, 7, 8, and 20-28; or combinations thereof.

A further embodiment of the present invention is a method for the serological detection of acute neuroborreliosis, comprising the use of peptide microarray comprising a collection or set of peptides comprising amino acid sequences shifted one residue across all of the peptides comprising the amino acid sequences of SEQ ID NOs: 1, 2, 4, 7, 8, and 20-28.

In further embodiments of the present invention, the method for the serological detection of exposure to and/or infection by one or more tick-borne pathogens in a sample from a subject, comprises: contacting the sample with at least one peptide which is reactive with, and specific for antibodies to the tick-borne pathogens comprising: at least one peptide comprising any one of the amino acid sequences in SEQ ID NOs: 1-19 and 29-43 and 60-97 as well as fragments and variants thereof (e.g., SEQ ID NOs: 98-110); or at least one collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof; and detecting the binding between the anti-TBD pathogen antibodies in the sample and the peptide or peptides.

In yet further embodiments of the present invention, the method for the serological detection of exposure to and/or infection by at least one tick-borne pathogen in a sample from a subject, comprises: contacting the sample with a peptide microarray comprising peptides which are reactive with, and specific for antibodies to tick-borne pathogens comprising: at least one peptide comprising any one of the amino acid sequences in SEQ ID NOs: 1-19 and 29-43 and 60-97 as well as fragments and variants thereof (e.g., SEQ ID NOs: 98-110); or at least one collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof; and detecting the binding between the anti-TBD pathogen antibodies in the sample and the peptide or peptides in the microarray.

In further embodiments of the present invention, the method for the diagnosis of acute neuroborreliosis, in a sample from a subject, comprises: contacting the sample with at least one peptide which is reactive with, and specific for antibodies to the tick-borne pathogens comprising: at least one peptide comprising any one of the amino acid sequences in SEQ ID NOs: 1, 2, 4, 7, 8, and 20-28; or at least one collection or set of peptides comprising amino acid sequences shifted one residue across at least one peptide comprising any one of the amino acid sequences in SEQ ID NOs: 1, 2, 4, 7, 8, and 20-28; or combinations thereof; and detecting the binding between the anti-TBD pathogen antibodies in the sample and the peptide or peptides.

In yet further embodiments of the present invention, the method for the diagnosis of acute neuroborreliosis in a sample from a subject, comprises: contacting the sample with a peptide microarray comprising peptides which are reactive with, and specific for antibodies to tick-borne pathogens comprising: at least one peptide comprising any one of the amino acid sequences in SEQ ID NOs: 1, 2, 4, 7, 8, and 20-28; or at least one collection or set of peptides comprising amino acid sequences shifted one residue across at least one peptide comprising any one of the amino acid sequences in SEQ ID NOs: 1, 2, 4, 7, 8, and 20-28; or combinations thereof; and detecting the binding between the anti-TBD pathogen antibodies in the sample and the peptide or peptides in the microarray.

The peptides, and collections and sets of peptides of the invention for the detection of the antibodies to the TBD pathogens can used in any number of immunodetection techniques, which include but are not limited to Western blot, enzyme-linked immunosorbent assay (ELISA), lateral flow, dipstick type of assay or a SNAP test, multiplex antibody detection techniques of various kinds, or any modification of such assays that are suitable for detecting antibodies of interest. Many suitable antibody detection methods are described including, for example, in U.S. Pat.

No. 9,034,656. In other embodiments, the detecting step comprises performing an agglutination assay. In other embodiments, the detecting step comprises spinning the sample in an analytical or centrifugal rotor. In still other embodiments, the detecting step comprises analyzing the sample with an electrochemical sensor, an optical sensor, or an opto-electronic sensor. In certain embodiments, the detecting step comprises performing a wavelength shift assay.

In one embodiment, the immunodetection technique is in the form of a programmable peptide array.

In certain embodiments, peptides of the invention are attached to or immobilized on a solid support. In one embodiment, the peptides of the invention are attached to a solid support through a metallic nanolayer. In certain embodiments, the solid support is a bead (e.g., a colloidal particle, metallic nanoparticle or nanoshell, or latex bead), a flow path in a lateral flow immunoassay device (e.g., a porous membrane), a blot (e.g., Western blot, a slot blot, or dot blot), a flow path in an analytical or centrifugal rotor, or a tube or well (e.g., in a plate suitable for an ELISA assay or microarray). In certain embodiments, the solid support comprises metal, glass, a cellulose-based material (e.g., nitrocellulose), or a polymer (e.g., polystyrene, polyethylene, polypropylene, polyester, nylon, or polysulfone).

In certain embodiments, peptides of the invention are isolated (e.g., synthetic and/or purified) peptides. In certain embodiments, peptides of the invention are conjugated to a ligand. For example, in certain embodiments, the peptides are biotinylated. In other embodiments, the peptides are conjugated to streptavidin, avidin, or neutravidin. In other embodiments, the peptides are conjugated to a carrier protein (e.g., serum albumin, keyhole limpet hemocyanin (KLH), or an immunoglobulin Fc domain).

The patient antibody or antibodies to TBD pathogens can be an IgG or IgM, or other immunoglobulin classes or subtypes.

The present invention also includes systems and kits for the serological detection of exposure to and/or infection by agents that cause TBD or for the diagnosis of acute neuroborreliosis.

Additionally, the invention provides for a method for the serological detection of Post-treatment Lyme Disease (PTLDS) and other stages of Lyme Disease, using at least one peptide or at least one collection or set of peptides which are reactive with, and specific for antibodies of various stages of Lyme Disease.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 1 shows the epitope identification using TBD-Serochip.

FIG. 2 shows the reproducibility of the peptide assay. This figure shows additional data for the C6 region of the VlsE protein of *B. burgdorferi*.

FIG. 3 shows the identification of the discriminatory epitopes for the diagnosis of babesiosis (infection by *Babesia microti*).

DETAILED DESCRIPTION OF THE INVENTION

Definitions

Figure 1A:
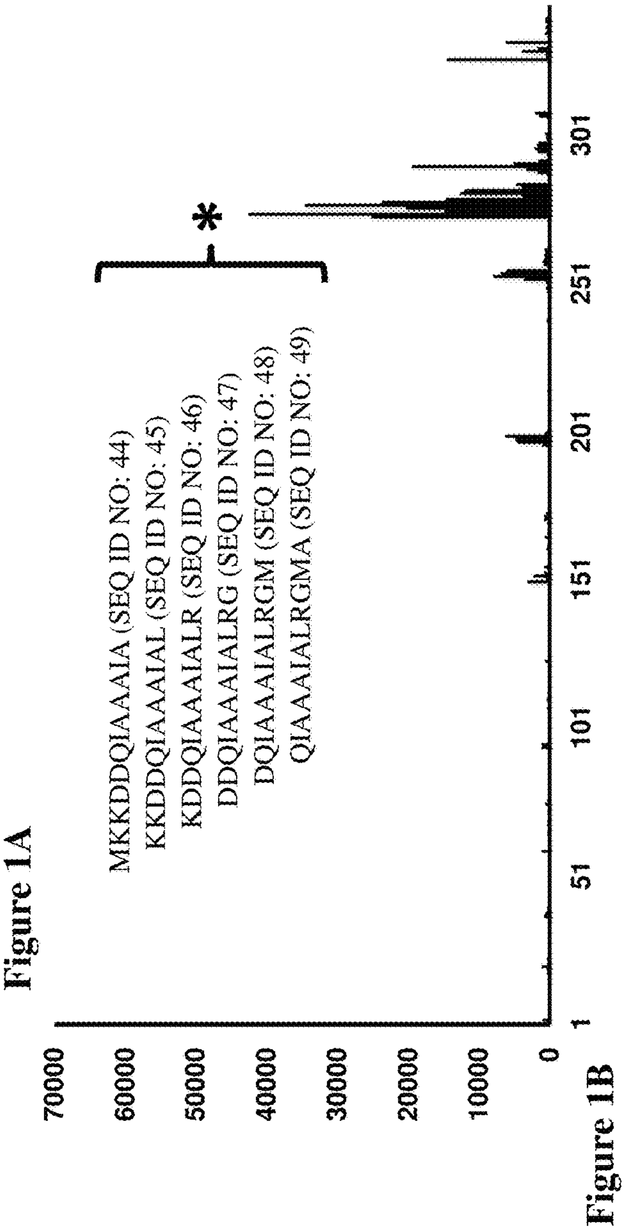
FIG. 1A shows the reactivity data generated for the C6 region of the *B. burgdorferi* VlsE antigen using patient sera from early acute Lyme disease (LD).

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

As used herein, the term "sample" means any substance containing or presumed to contain antibodies, in particular those to a pathogen or agent that can cause a tick-borne disease. The sample can be of natural or synthetic origin and can be obtained by any means known to those of skill in the art. The sample can be a sample of tissue or fluid isolated from a subject including but not limited to, plasma, serum, whole blood, cerebrospinal fluid (CSF), semen, amniotic fluid, lymph fluid, synovial fluid, urine, tears, blood cells, organs, and tissue. Samples can be research, clinical, or environmental. Sample can also be blood products used to transfuse or treat. Samples can also be synthetic and include but are not limited to in vitro cell culture constituents including but not limited to conditioned medium, recombinant cells, and cell components.

As used herein, the term "subject" means any organism including, without limitation, a mammal such as a fox, a deer, a mouse, a rat, a dog, a guinea pig, a ferret, a rabbit and a primate. In the preferred embodiment, the subject is a human being, a pet or livestock animal.

The term "patient" as used in this application means a human subject.

The term "tick-borne" means arising from a tick, usually from a bite. A "tick-borne disease" or "TBD" is a disease caused by a tick-borne pathogen or agent, which can be a virus or a bacterium.

The terms "detection", "detect", "detecting" and the like as used herein means as used herein means to discover the presence or existence of.

The terms "identification", "identify", "identifying" and the like as used herein means to recognize exposure to a specific pathogen or agent in sample from a subject.

The term "peptide" includes any sequence of two or more amino acids. Peptide sequences specifically recited herein are written with the amino terminus on the left and the carboxy terminus on the right.

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate, hippuric acid, octahydroindole-2-carboxylic acid, statine, 1,2,3,4,-tetrahydroisoquinoline-3-carboxylic acid, penicillamine, omithine, citruline, alpha-methylalanine, para-benzoylphenylalanine, phenylglycine, propargylglycine, sarcosine, and tert-butylglycine). The term also includes natural and unnatural amino acids bearing a conventional amino protecting group (e.g., acetyl or benzyloxycarbonyl), as well as natural and unnatural amino acids protected at the carboxy terminus (e.g., ($C_1$-$C_6$) alkyl, phenyl or benzyl ester or amide).

An "antigen" (from antibody-generating) or "immunogen" is a substance that prompts the generation of antibodies and can cause an immune response. They may also be used for diagnostic or patient selection or characterization purposes.

Antibodies (also known as immunoglobulins (Ig)) are gamma globulin proteins that are found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies are produced by B cells. There are several different types of antibody heavy chains, and several different kinds of antibodies, which are grouped into different isotypes based on which heavy chain they possess. Five different antibody isotypes are known in mammals, which perform different roles, and help direct the appropriate immune response for each different type of foreign object they encounter.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The part of the antigen recognized by an antibody is termed an "epitope." These epitopes bind with their antibody in a highly specific interaction, called induced fit, which allows antibodies to identify and bind only their specific epitope in the matching antigen(s) in the midst of the millions of different molecules that make up an organism. Recognition of an antigen by an antibody tags it for attack by other parts of the immune system. Antibodies can also neutralize targets directly by, for example, binding to a part of a pathogen that it needs to cause an infection. Production of antibodies is the main function of the humoral immune system.

As used herein, the term "isolated" and the like means that the referenced material is free of components found in the natural environment in which the material is normally found. In particular, isolated biological material is free of cellular components. An isolated peptide or protein may be associated with other proteins or nucleic acids, or both, with which it associates in the cell, or with cellular membranes if it is a membrane-associated protein. An isolated material may be, but need not be, purified.

The term "substantially purified," as used herein, refers to a molecule, such as a peptide, that is substantially free of cellular material (proteins, lipids, carbohydrates, nucleic acids), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The current invention enhances the differential diagnosis and management of tick-borne disease by establishing a new serologic assay platform.

In contrast to molecular diagnostics where advances in technology such as polymerase chain reaction and high-throughput screening have dramatically improved sensitivity, specificity and breadth over the past 20 years, serologic methods remained largely unchanged. This lag is important given the role of serology in establishing the distribution and frequency of infection, testing the significance of association between the finding of an agent and disease, and in focusing efforts in pathogen discovery.

The limitations of current platforms have prompted the exploration of alternative diagnostic tools for detection of TBDs. Described herein is the first sensitive, unbiased, highly multiplexed array-based assay or platform for diagnostic serology of tick-borne illnesses or disease using the peptides of the current invention, named Tick-borne Disease Serochip (TBD-Serochip). The TBD-Serochip offers substantial improvement in target selection by employing an extensive range of linear peptides that identifies key specific immunodominant epitopes. These peptides used in the TBD-Serochip are the key to the enhanced diagnostic accuracy, and provide a differential diagnosis not available with currently employed serologic assays for TBDs.

These peptides and the peptide array-based platform will enable new strategies for investigating the epidemiology and pathogenesis of acute and chronic diseases due to infection and for monitoring humoral responses to vaccines and immunomodulatory drugs. It will also serve as a screening tool for rapid selection of key informative peptides that can be used in established, inexpensive, alternative platforms including lateral flow immunoassays and ELISAs. Such applications will have practical utility for both clinical medicine and public health by enabling retrospective differential diagnosis of an infectious illness (when genetic footprints of the agent may no longer be present), and in facilitating outbreak investigation and surveillance.

This is particularly useful in infection by ticks as nucleic acid of the infective agents are transient and found in low levels in a patient's blood.

The array-based assay and peptides of the current invention have several advantages over serologic platforms currently employed for TBD diagnosis. First, its highly multiplexed format screens for multiple agents as opposed to the single agent test in ELISA, Western blot, and IFA. This is a substantial improvement, since *Ixodes scapularis* ticks alone can transmit at least five human pathogens and individual ticks are frequently infected with more than one agent. The presence of antibodies to multiple agents can be attributed to concurrent infections as well as asymptomatic, or past infections. The capacity of the assay and peptides of the invention to simultaneously detect both IgG and IgM can be helpful in extrapolating infection status. As shown in Examples, analysis of sera from patients with TBD (excluding the 10 known dual Lyme disease and babesiosis positive sera) showed antibodies to another agent in 26% of specimens. These findings, as well as recent work by others that revealed 29% of Lyme disease patients also had antibodies to *B. microti*, emphasize the critical need for a multiplex test for TBDs (Curcio et al. 2016).

Early detection of infection enables rapid and appropriate treatment, thereby reducing morbidity and the potential for progression to chronic disease. The assay and peptides of the current invention have advantages over existing diagnostic platforms in this regard. The peptides of the current invention include a wide range of specific peptides, including the first discriminatory epitopes for anaplasmosis and Powassan disease, as well as new diagnostic targets for Lyme disease and babesiosis. Both IgG and IgM can be detected simultaneously. The assay of the current invention also allows simultaneous detection and confirmation of infection. Whereas the current diagnostic algorithm for diagnosis of Lyme disease requires ELISA followed by confirmatory western blot, the assay of the current invention provides evidence of immunoreactivity to multiple epitopes in a single reaction. The peptides described herein can also readily be adapted to other serologic platforms, such as ELISA, Luminex or lateral flow immunoassays.

As new TBDs agents are discovered, the assay of the current invention is inherently more flexible than other platforms because new targets can be added to arrays through in situ peptide synthesis. Target protein selection, peptide design, and manufacture of an array or other assay comprising the peptides can be executed in less than 4 weeks, facilitating rapid development of new and specific diagnostic tests for novel TBDs agents.

In addition to its utility as a diagnostic platform, the peptides and assay of the current invention provides a powerful research tool for studies of TBDs as they can be employed to discriminate individual antibody responses in patients with TBD and thus examine the interplay of TBD agents on disease manifestation and progression. It can also be used to assess the impact of genetic diversity of tick-borne pathogens on the host immune response. The array can resolve antibodies to different genotypes of TBD agents, such as OspC types of *B. burgdorferi*, or analyze the temporal response to the multitude of *B. burgdorferi* VlsE or *A. phagocytophilum* MSP2 antigenic variants generated during the course of disease. It can also be utilized to identify potential changes in reactive epitopes in individuals with persistent symptoms following antibiotic treatment.

The current invention was developed using the strategy of tiling each antigen in a sliding window of 12-mer peptides that shifted one residue (e.g., residues 1-12, residues 2-13, residues 3-14, etc.). To ensure representation of a comprehensive antigenic profile, all protein variants were included in the 12-mer design for each antigen. The goal was to obtain peptides that are specific and sensitive for each antigen of the tick-borne pathogens or agents including *Borrelia burgdorferi, Borrelia miyamotoi, Babesia microti, Anaplasma phagocytophilum, Ehlichia chaffeensis, Rickettsia rickettsii*, Heartland virus, and Powassan virus. Such peptides were obtained. See Example 1 and Table 1. The same tiling strategy can be used to synthesize shorter peptides, (6, 7, 8, 9 or 10 amino acids in length) corresponding to the other regions of the antigenic regions.

Approximately 10% to 20% of individuals that receive antibiotic therapy for Lyme disease experience prolonged symptoms that can include fatigue, musculoskeletal pain, and neurocognitive problems (CDC 2015). In individuals where the symptoms persist for six months or longer, this condition is called Post-treatment Lyme Disease Syndrome (PTLDS) (CDC 2015).

Thus, an additional aspect of the current invention are peptides and peptide array platforms that are diagnostic of PTLDS, and other stages of disease.

Peptides Reactive with and Specific for Antibodies to Tick-Borne Pathogens

The present invention includes peptides, isolated and non-isolated, which are strongly reactive with, specific for, and sensitive to, antibodies to tick-borne pathogens including *Borrelia burgdorferi, Borrelia miyamotoi, Babesia microti, Anaplasma phagocytophilum, Ehlichia chaffeensis, Rickettsia rickettsii*, Heartland virus, and Powassan virus in a sample. These peptides can be used in any type of serological assay or platform to screen for the presence of antibodies to *Borrelia burgdorferi, Borrelia miyamotoi, Babesia microti, Anaplasma phagocytophilum, Ehlichia chaffeensis, Rickettsia rickettsii*, Heartland virus, and Powassan virus, and to determine if a subject has had an infection by, and/or exposure to, any of these tick-borne pathogens or agents. These peptides can also be used to test for and monitor humoral responses to vaccines and immunomodulatory drugs thus being useful for the development of treatment and preventative agents for any of these tick-borne agents. These peptides can also be used to monitor treatment and management of tick-borne illnesses including both acute TBD as well as persistent conditions such as post-treatment Lyme disease syndrome (PTLDS).

One embodiment of the present invention is each of the peptides listed in Table 1 which are specifically immunoreactive for the listed tick-borne pathogen or agent. In tests with sera from patients with Lyme disease and other tick-borne diseases, these specific and immunoreactive regions were shown to be useful for the serologic detection of the pathogens. See Examples 2-7. These peptides detect all early and late Lyme disease cases and unlike current methods for diagnosis of Lyme disease that require two consecutive tests (ELISA followed by Western blot), do so in one single step.

TABLE 1

Peptides of the Invention

| Antigen (*B. burgdorferi*) | Peptide sequence | Accession number (coordinates) | Antibody class target |
|---|---|---|---|
| VlsE | MKKDDQIAAAIALRGMA (SEQ ID NO: 1) | CAJ41626 (274-290) | IgG |
| FlaB-2 | VQEGVQQEGAQQP (SEQ ID NO: 2) | NC001318 (211-221) | IgG and IgM |
| | | NP_047005 (20-33) | IgM |
| OspC Nt* | NSGKDGNTSANSA (SEQ ID NO: 3) | CAA59253 (132-144) | IgM and IgG |
| OspC type K | KAILTTDAAKDKG (SEQ ID NO: 4) | | |
| OspC type M | AAILKTNGTKDKG (SEQ ID NO: 5) | AC94173 (133-145) | IgM and IgG |
| P100 | SDIDIDSLVTDKVVAA (SEQ ID NO: 6) | CAA54794 | IgG |
| BBK07 | SEKITKLTPEELENLAK (SEQ ID NO: 7) | NC001855 (52-68) | IgG |
| Bdr | DLENLEKQFDIKFD (SEQ ID NO: 8) | ACK75301 (46-53) | IgG |
| OppA | VAYNMYINGELDFL (SEQ ID NO: 9) | AAB97671 (242-255) | IgG |
| BBO03 | KFDKLENHPFLGYPYK (SEQ ID NO: 10) | ACL33989 (55-70) | IgG |
| BmpA | VGMTFRAQEGAFLTGY (SEQ ID NO: 29) | WP_002656850 (128-143) | IgM |
| Dbp-1 | DAFKDKKTGSGVSEN (SEQ ID NO: 30) | WP_010890380 (61-75) | IgM |
| Dbp1-2 | AAFKEDKTGSKVSEN (SEQ ID NO: 31) | WP_106017049 (64-78) | IgM |
| BB and *B. garini* FLAB-1 | VQEGAQQEGAQQP (SEQ ID NO: 72) | | |
| BB-OspCK3 | KAILITDAAKDKGAA (SEQ ID NO: 73) | | |
| BB-C6B | MKKDDQIAAAIVLRGMA (SEQ ID NO: 74) | | |

TABLE 1-continued

| Peptides of the Invention | |
|---|---|
| BB-OspC-NT3 | NSGKGGDSASTNPA (SEQ ID NO: 75) |
| BB-OspC-NT4 | SCNNSGKDGNTSANSA (SEQ ID NO: 76) |
| BB-OspC-C | NSVKELTSPVVAESP (SEQ ID NO: 77) |

| Antigen (*B. microti*) | Epitope sequence | Accession number (coordinates) | Antibody class target |
|---|---|---|---|
| SA-1 (BMN 1-9-1) | VLSAGGSGGNGGNG (SEQ ID NO: 11) | XP 012648767 (24-37) | IgG |
| SA-1 (BMN 1-9-2) | HQEQNNANDSSNPTG (SEQ ID NO: 12) | XP 012648767 (40-54) | IgG |
| SA-1 (BMN 1-9-3) | EKNKKFNENLVKIEKR (SEQ ID NO: 13) | XP 012648767 (118-133) | IgG |
| BMN 1-17-1 | GENDIIQPPWEDTAP (SEQ ID NO: 14) | AF68253 (43-57) | IgG |
| BMN 1-17-2 | NKSEKAERKSHDTQT (SEQ ID NO: 15) | AF68253 (138-152) | IgG |
| BMN 1-17-3 | RKEGHGKPNTNKSEKAERK (SEQ ID NO: 32) | AF68253 (128-146) | IgG |
| BMN 1-17-4 | HDKINKNKSGNAGIKSYDTQ (SEQ ID NO: 33) | AF68253 (164-183) | IgG |
| BMN 1-17-7 | NKNKSGKAGIKSHNTQTP (SEQ ID NO: 34) | AF68253 (296-313) | IgG |
| BMN 1-3 | GTGWPSEAGGPSEAGG (SEQ ID NO: 16) | AAF68236 (59-74) | IgG |
| BAB 3-1 | GTGWPSEAGGPSEAGG (SEQ ID NO: 91) | | |
| BAB 17-5 | NKSGNAGIKSYDT (SEQ ID NO: 92) | | |
| BAB 17-6 | EGESHKEYVAEKTKEIDE (SEQ ID NO: 93) | | |
| BAB 9-4 | EGHGKPNTNKSEKAERK (SEQ ID NO: 94) | | |

| Antigen (*A. phagocytophilum*) | Epitope sequence | Accession number (coordinates) | Antibody class target |
|---|---|---|---|
| MSP2 (P44) | FDWNTPDPRIGFKDNML (SEQ ID NO: 17) | WP_044108210 (75-91) | IgG |
| MSP2 (P44) | TSGKDIVQFAKAVEIS (SEQ ID NO: 18) | WP_044108210 (160-175) | IgG |
| MSPS | HRVVGDGVYDDLPAQLPTNN (SEQ ID NO: 78) | | |
| MSP-1-1 | FDWNTPDPDPRIG (SEQ ID NO: 79) | | |
| MSP7 | WNTPDPRIGFKDNML (SEQ ID NO: 80) | | |
| ANA 2-1 | RLVDDTSPAGRTKDT (SEQ ID NO: 95) | | |

TABLE 1-continued

Peptides of the Invention

| Antigen (*B. miyamotoi*) | Epitope sequence | Accession number (coordinates) | Antibody class target |
|---|---|---|---|
| Vsp1 | KKIKDAVEFAANVKE (SEQ ID NO: 35) | ADK37753 (52-66) | IgM |
| Vlp | GCNNGGGEDPQKFLTSI (SEQ ID NO: 36) | ALM31565 (8-24) | IgM and IgG |
| Vlp | AETKKEDIGKYFADIEKTMTL (SEQ ID NO: 37) | ALM31565 (51-60) | IgM and IgG |
| Vlp | TDGIEKAKDAAEIAIAPAV (SEQ ID NO: 38) | ALM31565 (222-240) | IgM and IgG |
| Vlp | NSNTKKSDVGVYFKKV (SEQ ID NO: 39) | AHH06031 (47-62) | IgM and IgG |
| Vlp | VTGADILQAIVKDNGEA (SEQ ID NO: 40) | AHH06031 (214-230) | IgM and IgG |
| Vlp | KTTTKKNDVGVYFNSLG (SEQ ID NO: 41) | AGS80213 (72-77) | IgM and IgG |
| Vlp | LKFAKGGSDAHLSNSAN (SEQ ID NO: 42) | AGS80213 (257-262) | IgM and IgG |
| FlaB | AQAAPAQEGAQQE (SEQ ID NO: 43) | AHH05270 (205-217) | IgM and IgG |
| C6F | IAAGIALRAMAKDGKFIVKD (SEQ ID NO: 81) | | |
| VSP | KKIKDAVEFAANV (SEQ ID NO: 82) | | |
| VSP2 | KKIKDAVEFAASV (SEQ ID NO: 83) | | |
| VLP-L | IGCNNGGGEDPQKVFLTSIA (SEQ ID NO: 84) | | |
| VMP 13 | KNIEEAKDAASIAAAKQT (SEQ ID NO: 85) | | |
| VMP14 | AKEENIAKASASIGAVSGA (SEQ ID NO: 86) | | |
| VMP15 | GIEQAKNAAEIAAAKN (SEQ ID NO: 87) | | |
| VMP 16 | TSEAKIETAKDAASI (SEQ ID NO: 88) | | |
| VMP21 | IEEAKDAASIAAAK (SEQ ID NO: 89) | | |
| VMP3 | SAAQNVKTAEELGM (SEQ ID NO: 96) | | |

| Antigen (Powassan virus) | Epitope sequence | Accession number (coordinates) | Antibody class target |
|---|---|---|---|
| Glycoprotein | EDLALPWKHKDNQDWN (SEQ ID NO: 19) | ADK37753 (499-514) | IgG |
| POW | EDLALPWKHKDNQDWN (SEQ ID NO: 90) | | |

TABLE 1-continued

| Peptides of the Invention | | | |
|---|---|---|---|
| Antigen (*E. chaffeensis*) | Peptide sequence | Accession number (coordinates) | Antibody class target |
| Ehl-Trp47 | NAVSQETPATQPQSRD (SEQ ID NO: 60) | | |
| Ehl-120-1 | QEKTNPEVLIKDLQDVASH (SEQ ID NO: 61) | | |
| Ehl-120-2 | QEETNPEVLIKDLQDVASH (SEQ ID NO: 62) | | |
| Ehl-120- | TNPEVLIKDLQDVASH (SEQ ID NO: 63) | | |
| Ehl-120-3 | KTNPEVLIKDLQDVA (SEQ ID NO: 64) | | |
| Ehl-SPRP | SAYVYCDKDGNEYFNTQSY (SEQ ID NO: 65) | | |
| Ehl-p28-1 | LYGLKQDWNGVSASSH (SEQ ID NO: 66) | | |
| Ehl-p28-5 | GVFGLKQDWDGSAIPHTQS (SEQ ID NO: 67) | | |
| Ehl-p28-6 | HVYTLKESPKVTSAVA (SEQ ID NO: 68) | | |
| Ehl-p28-7 | YNTTQLVGLKKDISVIGNSNIT (SEQ ID NO: 69) | | |
| Ehl-p28-8 | DTKQLVSYGKTPNSIDLKT (SEQ ID NO: 70) | | |
| Ehl-VPLT-1 | DLQQSSNSDLHGSFS (SEQ ID NO: 71) | | |
| Ehl-p28-9 | NTAQLVGLKKDISIT (SEQ ID NO: 97) | | |

*N terminal conserved region

A further embodiment includes fragments and variants of the peptides listed in Table 1. In some embodiments, the peptide has fewer amino acids than any peptide sequence listed in Table 1. In some embodiments, the peptide has about one less amino acid than any peptide sequence listed in Table 1. In some embodiments, the peptide has about two less amino acids than any peptide sequence listed in Table 1. In some embodiments, the peptide has about three less amino acids than any peptide sequence listed in Table 1. In some embodiments, the peptide has about four less amino acids than any peptide sequence listed in Table 1. In some embodiments, the peptide has about five less amino acids than any peptide sequence listed in Table 1. In some embodiments, the peptide has about six less amino acids than any peptide sequence listed in Table 1. In some embodiments, the peptide has about seven less amino acids than any peptide sequence listed in Table 1. In some embodiments, the peptide has more than about seven less amino acids than any peptide sequence listed in Table 1.

Examples of these peptides include the following:

(SEQ ID NO: 98)
LALPWKHKDNQDW,
portion of SEQ ID NO: 90;

-continued (SEQ ID NO: 99)
HQEQNNANDSSNPT,
portion of SEQ ID NO: 12;

(SEQ ID NO: 100)
NKSGKAGIKSHNTQT,
portion of SEQ ID NO: 34;

(SEQ ID NO: 101)
TNPEVLIKDLQDVA,
portion of SEQ ID NO: 63;

(SEQ ID NO: 102)
YVYCDKDGNEYFNT,
portion of SEQ ID NO: 65;

(SEQ ID NO: 103)
LYGLKQDWNGVS,
portion of SEQ ID NO: 66;

(SEQ ID NO: 104)
QQSSNSDLHGSFS,
portion of SEQ ID NO: 71;

(SEQ ID NO: 105)
VGMTFRAQEGAF,
portion of SEQ ID NO: 29;

(SEQ ID NO: 106)
KITKLTPEELENL,

-continued portion of SEQ ID NO: 7;

(SEQ ID NO: 107)
TSGKDIVQFAKAV,
portion of SEQ ID NO: 18;

(SEQ ID NO: 108)
KKIKDAVEFAA,
portion of SEQ ID NO: 83;

(SEQ ID NO: 109)
IEEAKDAASIAA,
portion of SEQ ID NO: 85;
and (SEQ ID NO: 110)
CNNGGGEDPQKVFL,
portion of SEQ ID NO: 84.

In some embodiments, variants of any of the peptides listed in Table 1 include but are not limited to, sequences having at least from about 50% to about 55% identity to that of any of the peptide sequences listed in Table 1. In some embodiments, variants of any of the peptides listed in Table 1 include but are not limited to, sequences having at least from about 55.1% to about 60% identity to that of any of the peptide sequences listed in Table 1. In some embodiments, variants of any of the peptides listed in Table 1 include but are not limited to, sequences having at least from about 60.1% to about 65% identity to that of any of the peptide sequences listed in Table 1. In some embodiments, variants of any of the peptides listed in Table 1 include but are not limited to, sequences having at least from about 65.1% to about 70% identity to that of any of the peptide sequences listed in Table 1. In some embodiments, variants of any of the peptides listed in Table 1 include but are not limited to, sequences having at least from about 70.1% to about 75% identity to that of any of the peptide sequences listed in Table 1. In some embodiments, variants of any of the peptides listed in Table 1 include but are not limited to, sequences having at least from about 75.1% to about 80% identity to that of any of the peptide sequences listed in Table 1. In some embodiments, variants of any of the peptides listed in Table 1 include but are not limited to, sequences having at least from about 80.1% to about 85% identity to that of any of the peptide sequences listed in Table 1. In some embodiments, variants of any of the peptides listed in Table 1 include but are not limited to, sequences having at least from about 85.1% to about 90% identity to that of any of the peptide sequences listed in Table 1. In some embodiments, variants of any of the peptides listed in Table 1 include but are not limited to, sequences having at least from about 90.1% to about 95% identity to that of any of the peptide sequences listed in Table 1.

A further embodiment of the present invention is a collection or set of isolated peptides comprising two or more up to all of the amino acid sequences listed in Table 1 (SEQ ID NOs 1-19 and 29-43 and 60-97) and fragments and variants thereof.

A further embodiment of the present invention comprises a collection or set of peptides comprising amino acid sequences shifted one residue across any of the peptides listed in Table 1 (SEQ ID NOs: 1-19 and 29-43 and 60-97) and fragments and variants thereof. For example, see FIG. 1 (SEQ ID NOs: 44-49), FIG. 2D (SEQ ID NOs: 44-52), and FIG. 5 (SEQ ID NOs: 53-59).

A further embodiment of the present invention is a collection or set of isolated peptides shifted one residue across all of the peptides listed in Table 1 (SEQ ID NOs: 1-19 and 29-43 and 60-97).

A further embodiment is a collection or set of peptides comprising peptides with the amino acid sequences SEQ ID NOs: 1, 2, 11, 15, 30, 31, 43, 60, 73, 80, and 95-110. A further embodiment comprises a collection or set of peptides comprising amino acid sequences shifted one residue across any of the peptide with the amino acid sequences SEQ ID NOs: 1, 2, 11, 15, 30, 31, 43, 60, 73, 80, and 95-110. A further embodiment is a collection or set of isolated peptides shifted one residue across all of the peptides with the amino acid sequences SEQ ID NOs: 1, 2, 11, 15, 30, 31, 43, 60, 73, 80, and 95-110.

A further embodiment of the present invention is each of the isolated peptides listed in Table 6 which are specific for the listed epitopes of *Borrelia burgdorferi*, and of particular usefulness in the diagnosis of acute neuroborreliosis.

A further embodiment of the present invention is a collection or set of isolated peptides comprising two or more up to all 14 amino acid sequences listed in Table 6 (SEQ ID NOs: 1, 2, 4, 7, 8, and 20-28) and fragments and variants thereof.

A further embodiment of the present invention is a collection or set of isolated peptides shifted one residue across at least one of the peptides listed in Table 6 (SEQ ID NOs: 1, 2, 4, 7, 8, and 20-28) and fragments and variants thereof.

A further embodiment of the present invention is a collection or set of isolated peptides shifted one residue across all of the peptides listed in Table 6 (SEQ ID NOs: 1, 2, 4, 7, 8, and 20-28) and fragments and variants thereof.

These collections or sets can comprise isolated peptides that are 6 amino acids in length, 7 amino acids in length, 8 amino acids in length, 9 amino acids in length, 10 amino acids in length, 11 amino acids in length, and up to 12 amino acids in length.

Peptides of 12 amino acids are preferred based upon work that shows that antibodies bind to linear peptide sequences ranging from 5 to 9 amino acids in length and bind most efficiently when targets are flanked by additional amino acids (Buus et al. 2012). However, peptides containing less than 12 amino acids in length and more than 12 amino acids in length can be used. Peptides 13 amino acids in length, 14 amino acids in length, 15 amino acids in length, 16 amino acids in length, 17 amino acids in length, 18 amino acids in length, 19 amino acids in length, 20 amino acids in length, up to 25 amino acids in length, up to 30 amino acids in length, up to 35 amino acids in length, up to 40 amino acids in length, and up to 50 amino acids in length can be used.

In certain embodiments, peptides of the invention are produced by synthetic chemistry (i.e., a "synthetic peptide"). In other embodiments, peptides of the invention are produced biologically. An isolated peptide of the invention can be in water, a buffer, or in a dry form awaiting reconstitution, e.g., as part of a kit. An isolated peptide of the present invention can be in the form of a pharmaceutically acceptable salt. Suitable acids and bases that are capable of forming salts with the peptides of the present invention are well known to those of skill in the art, and include inorganic and organic acids and bases.

In certain embodiments, peptides of the invention are modified. The peptides of the invention may be modified by a variety of techniques, such as by denaturation with heat and/or a detergent (e.g., SDS). Alternatively, peptides of the invention may be modified by association with one or more further moieties. The association can be covalent or non-covalent, and can be, for example, via a terminal amino acid linker, such as lysine or cysteine, a chemical coupling agent, or a peptide bond. The additional moiety can be, for example, a ligand, a ligand receptor, a fusion partner, a detectable label, an enzyme, or a substrate that immobilizes the peptide.

Peptides of the invention can be conjugated to a ligand, such as biotin (e.g., via a cysteine or lysine residue), a lipid molecule (e.g., via a cysteine residue), or a carrier protein (e.g., serum albumin, immunoglobulin Fc domain, keyhole limpet hemocyanin (KLH) via e.g., a cysteine or lysine residue). Attachment to ligands, such as biotin, can be useful for associating the peptide with ligand receptors, such as avidin, streptavidin, polymeric streptavidin, or neutravidin. Avidin, streptavidin, polymeric streptavidin, or neutravidin, in turn, can be linked to a signaling moiety (e.g., an enzyme, such as horse radish peroxidase (HRP) or alkaline phosphatase (ALP), or other moiety that can be visualized, such as a metallic nanoparticle or nanoshell (e.g., colloidal gold) or a fluorescent moiety), or a solid substrate (e.g., nitrocellulose membrane). Alternatively, the peptides of the invention can be fused or linked to a ligand receptor, such as avidin, streptavidin, polymeric streptavidin, or neutravidin, thereby facilitating the association of the peptides with the corresponding ligand, such as biotin and any moiety (e.g., signaling moiety) or solid substrate attached thereto. Examples of other ligand-receptor pairs are well-known in the art and can similarly be used.

Peptides of the invention can be fused to a fusion partner (e.g., a peptide or other moiety) that can be used to improve purification, to enhance expression of the peptide in a host cell, to aid in detection, and to stabilize the peptide. Examples of suitable compounds for fusion partners include carrier proteins (e.g., serum albumin, immunoglobulin Fc domain, KLH), and enzymes (e.g., horse radish peroxidase (HRP), beta-galactosidase, glutathione-S-transferase, alkaline phosphatase). The fusion can be achieved by means of a peptide bond. For example, peptides of the invention and fusion partners can be fusion proteins and can be directly fused in-frame or can comprise a peptide linker.

In addition, peptides of the invention may be modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, and transfer-RNA mediated addition of amino acids to proteins such as arginylation. Analogues of an amino acid (including unnatural amino acids) and peptides with substituted linkages are also included. Peptides of the invention that consist of any of the sequences discussed herein may be modified by any of the discussed modifications. Such peptides still "comprise" or "consist of" the amino acids.

Modifications as set forth above are well-known to those of skill in the art and have been described in great detail in the scientific literature.

Nucleic Acids Comprising a Sequence Encoding the Peptides Reactive with and Specific for Antibodies to Tick-Borne Pathogens In another aspect, the invention provides nucleic acids comprising a sequence encoding a peptide of the invention. Nucleic acids of the invention can be single- or double-stranded. A nucleic acid can be RNA, DNA, cDNA, genomic DNA, chemically synthesized RNA or DNA or combinations thereof. The nucleic acids can be purified free of other components, such as proteins, lipids and other polynucleotides. For example, the nucleic acids can be 50%, 75%, 90%, 95%, 96%, 97%, 98%, 99%, or 100% purified. The nucleic acids of the invention encode the peptides described herein. In certain embodiments, the nucleic acids encode a peptide having the sequence of SEQ ID NOs: 1-110. Nucleic acids of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Methods for preparing polynucleotides operably linked to an expression control sequence and expressing them in a host cell are well-known in the art. See, e.g., U.S. Pat. No. 4,366,246. A nucleic acid of the invention is operably linked when it is positioned adjacent to or close to one or more expression control elements, which direct transcription and/or translation of the polynucleotide.

Thus, for example, the peptides of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably linked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al., Molecular Cloning, A Laboratory Manual, current edition, Cold Spring Harbor Laboratory, New York; Miller et al, Genetic Engineering, 8:277-298 (Plenum Press, current edition), Wu et al., Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al., Eds.) John Wiley & Sons, NY (current edition), and references cited therein.

Accordingly, the invention also provides vectors comprising nucleic acids of the invention, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

Platforms, Assays, and Devices

It should be understood by one of skill in the art that any number of conventional protein assay formats, particularly immunoassay formats, may be designed to utilize the isolated peptides of this invention, and collections and sets of peptides of the invention, for the detection of antibodies to tick-borne pathogens in a subject. This invention is thus not limited by the selection of the particular assay format, and is believed to encompass assay formats that are known to those of skill in the art. Thus, the peptides of the present invention can be used in any assay, format or platform for antibody detection including but not limited to ELISA, Luminex, Western blot assays, immunofluorescence assays, and spotted peptide arrays, as well as those platforms that are later developed.

In certain embodiments of the invention, the assay comprises: immobilizing the antibody(s) in the sample; adding a peptide of the invention; and detecting the degree of antibody bound to the peptide, e.g., by the peptide being labeled or by adding a labeled substance, such as a labeled binding partner (e.g., streptavidin-HRP or streptavidin-colloidal gold complex) or a labeled antibody which specifically recognizes the peptide.

In other embodiments, the assay comprises: immobilizing a peptide of the invention; adding the sample containing antibodies; and detecting the amount of antibody bound to the peptide, e.g., by adding another peptide of the invention conjugated, directly or indirectly, to a label (e.g., metallic nanoparticle or metallic nanoshell, fluorescent label, or enzyme (e.g., horseradish peroxidase or alkaline phosphatase)) or by adding a labeled substance, such as a binding partner or a labeled antibody which specifically recognizes the sample antibodies (e.g., anti-human IgG antibodies, or anti-human IgM antibodies).

In other embodiments, the assay comprises: immobilizing a peptide of the invention; adding the sample containing antibodies; and detecting the amount of antibody bound to the peptide, e.g., by adding a first binding partner which specifically recognizes the sample antibodies (e.g., anti-human IgG antibodies, or anti-human IgM antibodies), and further adding a second binding partner, wherein the second binding partner is labeled and recognizes said first binding partner.

In still other embodiments, the assay comprises: reacting the peptide and the sample containing antibodies without any of the reactants being immobilized, and then detecting the amount of complexes of antibody and peptide, e.g., by the peptide being labeled or by adding a labeled substance, such as a labeled binding partner (e.g., streptavidin-HRP or streptavidin-colloidal gold complex) or a labeled antibody which specifically recognizes the peptide.

Immobilization of a peptide of the invention can be either covalent or non-covalent, and the non-covalent immobilization can be non-specific (e.g., non-specific binding to a polystyrene surface in a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, for example, a biotin or biotinyl group or an analogue thereof bound to an amino acid group of the peptide, and the component is then avidin, streptavidin, neutravidin, or an analogue thereof.

Suitable carriers, supports, and surfaces include, but are not limited to, metallic nanolayers, beads (e.g., magnetic beads, colloidal particles or metallic nanoparticles or nanoshells, such as colloidal gold, or particles or nanoparticles comprising silica, latex, polystyrene, polycarbonate, or PDVF), latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used.

Devices for performing specific binding assays, especially immunoassays, are known and can be readily adapted for use in the present methods. Solid-phase assay devices include microtiter plates, flow-through assay devices (e.g., lateral flow immunoassay devices), dipsticks, and immunocapillary or immunochromatographic immunoassay devices.

In some embodiments of the invention, the solid or semi-solid surface or carrier is the floor or wall in a microtiter well, a filter surface or membrane (e.g., a nitrocellulose membrane or a PVDF (polyvinylidene fluoride) membrane), a hollow fiber, a beaded chromatographic medium (e.g., an agarose or polyacrylamide gel), a magnetic bead, a fibrous cellulose matrix, an HPLC matrix, an FPLC matrix, a substance having molecules of such a size that the molecules with the peptide bound thereto, when dissolved or dispersed in a liquid phase, can be retained by means of a filter, a substance capable of forming micelles or participating in the formation of micelles allowing a liquid phase to be changed or exchanged without entraining the micelles, a water-soluble polymer, or any other suitable carrier, support or surface.

In some embodiments of the invention, the peptide of the invention is provided with a suitable label which enables detection. Conventional labels may be used which are capable, alone or in concert with other compositions or compounds, of providing a detectable signal. Suitable labels include, but are not limited to, enzymes (e.g., HRP, beta-galactosidase, or alkaline phosphatase), fluorescent labels, radioactive labels, colored latex particles, and metal-conjugated labels (e.g., metallic nanolayers, metallic nanoparticle- or metallic nanoshell-conjugated labels). Suitable metallic nanoparticle or metallic nanoshell labels include, but are not limited to, gold particles, silver particles, copper particles, platinum particles, cadmium particles, composite particles, gold hollow spheres, gold-coated silica nanoshells, and silica-coated gold shells. Metallic nanolayers suitable for detectable layers include nanolayers comprised of cadmium, zinc, mercury, and noble metals, such as gold, silver, copper, and platinum.

Suitable detection methods include, but are not limited to, detection of an agent which is tagged, directly or indirectly, with a colorimetric assay (e.g., for detection of HRP or beta-galactosidase activity), visual inspection using light microscopy, immunofluorescence microscopy, including confocal microscopy, or by flow cytometry (FACS), autoradiography (e.g., for detection of a radioactively labeled agent), electron microscopy, immunostaining, subcellular fractionation, or the like. In one embodiment, a radioactive element (e.g., a radioactive amino acid) is incorporated directly into a peptide chain. In another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody or other binding agent (e.g., protein A, protein G, protein L or combinations thereof) which binds to the first antibody. This secondary antibody or other binding agent can be labeled with, for example, a radioactive, enzymatic, fluorescent, luminescent, metallic nanoparticle or metallic nanoshell (e.g. colloidal gold), or other detectable label, such as an avidin/biotin system. In another embodiment, the binding partner is a peptide of the invention, which can be conjugated directly or indirectly to an enzyme, such as horseradish peroxidase or alkaline phosphatase or other signaling moiety. In such embodiments, the detectable signal is produced by adding a substrate of the enzyme that produces a detectable signal, such as a chromogenic, fluorogenic, or chemiluminescent substrate.

In some embodiments of the invention, the detection procedure comprises visibly inspecting the antibody-peptide complex for a color change or inspecting the antibody-peptide complex for a physical-chemical change. Physical-chemical changes may occur with oxidation reactions or other chemical reactions. They may be detected by eye, using a spectrophotometer, or the like.

One assay format is a lateral flow immunoassay format. Antibodies to human or animal immunoglobulins, can be labeled with a signal generator or reporter (e.g., colloidal gold) that is dried and placed on a glass fiber pad (sample application pad or conjugate pad). The diagnostic peptide is immobilized on membrane, such as nitrocellulose or a PVDF (polyvinylidene fluoride) membrane. When a sample is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide are present, they bind to the diagnostic peptide striped on the membrane, thereby generating a signal (e.g., a band that can be seen or visualized). An additional antibody specific to the labeled antibody or a second labeled antibody can be used to produce a control signal.

An alternative format for the lateral flow immunoassay comprises the peptides or compositions of the invention being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM or anti-animal IgG/IgM antibodies of the invention are immobilized on a membrane, such as nitrocellulose of PVDF, at a test site. When a sample is added to the sample application pad, antibodies in the sample react with the labeled peptide complexes such that antibodies that bind to peptides of the invention become indirectly labeled. The antibodies in the sample are then transported into the next membrane (PVDF or nitrocellulose containing the diagnostic peptide) by capillary action and bind to the immobilized anti-human IgG/IgM or anti-animal IgG/IgM antibodies. If any of the sample antibodies are bound to the labeled peptides of the invention, the label associated with the peptides can be seen or visualized at the test site.

Another assay for the screening of blood products or other physiological or biological fluids is an enzyme linked immunosorbent assay, i.e., an ELISA. Typically in an ELISA, isolated peptides or collection or set of peptides of the invention, are adsorbed to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody that is conjugated to an enzyme or other label by standard procedures and is dissolved in blocking buffer. The label can be chosen from a variety of enzymes, including horseradish peroxidase (HRP), beta-galactosidase, alkaline phosphatase (ALP), and glucose oxidase. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). Conditions for performing ELISA assays are well-known in the art.

In another embodiment of an ELISA, a peptide or a collection or set of peptides of the invention are immobilized on a surface, such as a ninety-six-well ELISA plate A sample is then added and the assay proceeds as above.

In still other embodiments, a peptide or collection or set of peptides of the invention are electro- or dot-blotted onto nitrocellulose paper. Subsequently, a sample, such as a biological fluid is incubated with the blotted antigen, and antibody in the sample is allowed to bind to the antigen(s). The bound antibody can then be detected, e.g., by standard immunoenzymatic methods or by visualization using metallic nanoparticles or nanoshells coupled to secondary antibodies or other antibody binding agents or combinations thereof.

Spotted arrays and these other platforms use similar protocols. After an initial blocking step, a serum sample is added to each platform. Following incubation and wash with mild detergent, a labeled secondary antibody (αIgG or αIgM) is added to detect primary antibodies bound to the array. The slide is washed and then scanned to quantitate fluorescent signal associated with immunoreactive peptides.

To date most serology has been performed using single-plex ELISA, complement fixation or neutralization assays. More recently, Luminex-based systems have been employed that can address up to 100 antigenic targets simultaneously (i.e., 100 individual pathogens, 100 individual antigenic targets for one pathogen, or some variation thereof) (Anderson et al. 2011). Additionally, arrays are established that comprise spotted recombinant proteins expressed in vitro in *E. coli, S. cerevesiae*, baculoviruses, or cell-free, coupled transcription-translation systems (Vigil et al. 2010).

One goal of the present invention is to automate the process of tick-borne disease detection and make it inexpensive, quick and accurate as well as detect exposure per se rather than to rigorously characterize humoral responses to specific pathogens.

One assay that meets these requirements is a programmable peptide array.

One method to create and validate a programmable array that can measure the humoral immune response to tick-borne pathogens, thus enabling detection of exposure to a tick-borne pathogen (or its gene products in vaccines), comprises the following steps: 1) select peptides using bioinformatic methods; 2) test those peptides printed on arrays for sensitivity and specificity using sera from humans and other animals who have been exposed to antigens of tick-borne pathogens; 3) examine the performance of algorithms typically employed for epitope prediction; 4) use assay results to develop smaller and less comprehensive peptide libraries that can be deployed in smaller and more facile platforms; 5) optimize and validate assay protocols; and 6) develop software to automate assay analysis.

Using these steps, the peptides of the present invention were generated. Using these steps, additional specific peptide which are strongly reactive with, and specific for antibodies to tick-borne pathogens, those listed herein as well as others, can be generated and used in all of the assays and methods disclosed herein.

Studies using subarrays to address the influence on sensitivity and specificity of blocking reagents, incubation conditions, and secondary antibody type and concentration have been done. Twelve subarrays have been printed on a single slide, each with a 172,000-feature capacity. Only minor adjustments in reagent concentrations and reaction conditions will be needed to optimize sensitivity and specificity. Materials and methods for assays with different sample sources (human vs nonhuman primate vs other phyla), sample types (serum vs plasma vs cerebrospinal fluid) and antibody isotype can be optimized.

The array capacity can be exploited to print multiple arrays per glass slide (configurations of 1, 3, 8, or 12 arrays can be printed).

A further embodiment of the present invention is a peptide microarray comprising peptides that are reactive with, and specific for antibodies to tick-borne pathogens. In some embodiments the peptide microarray comprises: at least one peptide comprising any one of the amino acid sequences in SEQ ID NOs: 1-19 and 29-43 and 60-97 as well as fragments and variants thereof; or a collection or set of peptides comprising amino acid sequences shifted one residue across at least one peptide comprising any one of the amino acid sequences in SEQ ID NOs: 1-19 and 29-43 and 60-97 as well as fragments and variants thereof; or combinations thereof. In some embodiments the peptide array comprises a set or collection of peptides, comprising amino acid sequences shifted one residue across all of the peptides comprising the amino acid sequences of SEQ ID NOs: 1-19 and 29-43 and 60-97.

Another embodiment of the present invention is a peptide microarray comprising peptides that are reactive with, and specific for antibodies to *Borrelia burgdorferi*. In some embodiments the peptide microarray comprises: at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof. In some embodiments the peptide array comprises a set or collection of peptides, comprising amino acid sequences shifted one residue across all of the peptides comprising the amino acid sequences of SEQ ID NOs: 1, 2, 4, 7, 8, and 20-28.

In some embodiments, these peptide microarrays are programmable.

Methods and Systems for Serological Detection of Exposure to and/or Infection by Tick-borne Pathogens The present invention includes methods and systems for the detection of exposure to and/or infection by tick-borne pathogens, i.e., antibodies to tick-borne pathogens including, but not limited to, *Borrelia burgdorferi, Borrelia miyamotoi, Babesia microti, Anaplasma phagocytophilum, Ehlichia chaffeensis, Rickettsia rickettsii*, Heartland virus, and Powassan virus, in any sample utilizing the various peptides, isolated and non-isolated, and peptide arrays of the present invention. The present invention also includes methods and systems for the diagnosis of acute neuroborreliosis Suitable methods typically include: receiving or obtaining (e.g., from a patient) a sample of bodily fluid or tissue likely to contain antibodies; contacting (e.g., incubating or reacting) a sample to be assayed with a peptide or peptides of the invention, under conditions sufficient for the formation of a specific peptide-antibody complex (e.g., for specific binding of the peptide to the antibody); and assaying the contacted (reacted) sample for the presence of an antibody-peptide reaction (e.g., determining the amount of an antibody-peptide complex). The presence of an elevated amount of the antibody-peptide complex indicates that the subject was exposed to and infected by a tick-borne pathogen. A peptide, including a modified form thereof, which "binds specifically" to an antibody against a tick-borne pathogen antigen interacts with the antibody, or forms or undergoes a physical association with it, in an amount and for a sufficient time to allow detection of the antibody.

Conditions for reacting peptides and antibodies so that they react specifically are well-known to those of skill in the art. See, e.g., Current Protocols in Immunology (Coligan et al., editors, John Wiley & Sons, Inc).

The methods and systems of the present invention may be used to detect exposure to antigens of tick-borne pathogens in research and clinical settings.

A preferred sample is a biological sample. A biological sample may be obtained from a tissue of a subject or bodily fluid from a subject including but not limited to nasopharyngeal aspirate, blood, cerebrospinal fluid, saliva, serum, plasma, urine, sputum, bronchial lavage, pericardial fluid, or peritoneal fluid, or a solid such as feces. The preferred sample is serum, plasma and cerebrospinal fluid (CSF). The subject may be any animal, particularly a vertebrate and more particularly a mammal, including, without limitation, a cow, dog, human, monkey, mouse, pig, deer, fox, or rat. In one embodiment, the subject is a human.

A sample may also be a research, clinical, or environmental sample.

Additional applications include, without limitation, detection of the screening of blood products (e.g., screening blood products for infectious agents), biodefense, food safety, environmental contamination, forensics, and genetic-comparability studies. The present invention also provides methods and systems for detecting antibodies in cells, cell culture, cell culture medium and other compositions used for the development of pharmaceutical and therapeutic agents.

A sample may also be a research, clinical, or environmental sample, such as cells, cell culture, cell culture medium, and compositions for use as, or the development of pharmaceutical and therapeutic agents.

Additional applications include, without limitation, detection of the screening of blood products (e.g., screening blood products for infectious agents), biodefense, food safety, environmental contamination, forensics, and genetic-comparability studies. The present invention also provides methods and systems for detecting viral antibodies in cells, cell culture, cell culture medium and other compositions used for the development of pharmaceutical and therapeutic agents.

The subject may have been exposed to antigens of tick-borne pathogens, suspected of having exposure to antigens of tick-borne pathogens or believed not to have had exposure to antigens of tick-borne pathogens. In one embodiment, the subject may have been found to be seropositive by tick-borne pathogen ELISA. In a further embodiment, the subject has been previously diagnosed with a tick-borne disease. In some embodiments, the tick-borne disease is Lyme disease.

In one embodiment, the subject may be a test subject, which has been administered a tick-borne pathogen vaccine or immunomodulatory agent.

The systems and methods described herein support the detection and measure of a humoral immune response to tick-borne pathogens.

Thus, one embodiment of the present invention provides a system for the detection of exposure to and/or infection of tick-borne pathogens, i.e., antibodies to tick-borne pathogens, in any sample. The system includes at least one subsystem wherein the subsystem includes a peptide or peptides which are reactive with, and specific for tick-borne pathogens antibodies, comprising: at least one peptide comprising any one of the amino acid sequences in SEQ ID NOs: 1-19 and 29-43 and 60-97 as well as fragments and variants thereof; or a collection or set of peptides comprising amino acid sequences shifted one residue across at least one peptide comprising any one of the amino acid sequences in SEQ ID NOs: 1-19 and 29-43 and 60-97 as well as fragments and variants thereof; or combinations thereof. The system can also include additional subsystems for the purpose of: preparation of the sample; binding of any tick-borne pathogens antibody in the sample with the peptides(s); washing the unbound sample; and visualization and/or quantification of bound antibody or antibodies.

A further embodiment of the present invention provides a system for the detection of exposure to and/or infection by tick-borne pathogens, i.e., antibodies to tick-borne pathogens, in any sample. The system includes at least one subsystem wherein the subsystem includes a peptide microarray comprising at least one peptide comprising any one of the amino acid sequences in SEQ ID NOs: 1-19 and 29-43 and 60-97 as well as fragments and variants thereof; or a collection or set of peptides comprising amino acid sequences shifted one residue across at least one peptide comprising any one of the amino acid sequences in SEQ ID NOs: 1-19 and 29-43 and 60-97 as well as fragments and variants thereof; or combinations thereof. The system can also include additional subsystems for the purpose of: preparation of the sample; binding of any tick-borne pathogens antibody in the sample with the peptides(s); washing the unbound sample; and visualization and/or quantification of bound antibody or antibodies.

The present invention provides a method for detecting the exposure to and/or infection by tick-borne pathogens, i.e., antibodies to tick-borne pathogens, in any sample, including the steps of: contacting the sample with a peptide or peptides which are reactive with, and specific for tick-borne pathogens antibodies, comprising: at least one peptide comprising any one of the amino acid sequences in SEQ ID NOs: 1-19 and 29-43 and 60-97 as well as fragments and variants thereof; or a collection or set of peptides comprising amino acid sequences shifted one residue across at least one peptide comprising any one of the amino acid sequences in SEQ ID NOs: 1-19 and 29-43 and 60-97 as well as fragments and variants thereof; or combinations thereof, under conditions sufficient for any antibodies to tick-borne pathogens in the sample and the peptides to bind; and visualizing and/or quantifying any bound antibody or antibodies to the peptides. The method may optionally include a step for washing any unbound sample.

The present invention provides a method for the detecting the exposure to and/or infection by tick-borne pathogens, i.e., antibodies to tick-borne pathogens, in any sample, including the steps of: contacting the sample with a peptide microarray comprising at least one peptide comprising any one of the amino acid sequences in SEQ ID NOs: 1-19 and 29-43 and 60-97 as well as fragments and variants thereof; or a collection or set of peptides comprising amino acid sequences shifted one residue across at least one peptide comprising any one of the amino acid sequences in SEQ ID NOs: 1-19 and 29-43 and 60-97 as well as fragments and variants thereof; or combinations thereof under conditions sufficient for any antibodies to tick-borne pathogens in the sample and the peptides to bind; and visualizing and or quantifying any bound antibody or antibodies to the peptides. The method may optionally include a step for washing any unbound sample.

A further embodiment of the present invention provides a system for the diagnosis of acute neuroborreliosis by the detection of exposure to antigens of *Borrelia burgdorferi*, in any sample. The system includes at least one subsystem wherein the subsystem includes a peptide or peptides which are reactive with, and specific for *Borrelia burgdorferi* antibodies, comprising: at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof. The system can also include additional subsystems for the purpose of: preparation of the sample; binding of any *Borrelia burgdorferi* antibody in the sample with the peptides(s); washing the unbound sample; and visualization and/or quantification of bound antibody or antibodies.

A further embodiment of the present invention provides a system for the diagnosis of acute neuroborreliosis by the detection of exposure to antigens of *Borrelia burgdorferi*, in any sample. The system includes at least one subsystem wherein the subsystem includes a peptide microarray comprising at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof. The system can also include additional subsystems for the purpose of: preparation of the sample; binding of any *Borrelia burgdorferi* antibody in the sample with the peptides(s); washing the unbound sample; and visualization and/or quantification of bound antibody or antibodies.

The present invention provides a method for the diagnosis of acute neuroborreliosis by the detection of exposure to antigens of *Borrelia burgdorferi*, in any sample, including the steps of: contacting the sample with a peptide or peptides which are reactive with, and specific for *Borrelia burgdorferi* antibodies, comprising: at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof, under conditions sufficient for any antibodies to *Borrelia burgdorferi* in the sample and the peptides to bind; and visualizing and/or quantifying any bound antibody or antibodies to the peptides. The method may optionally include a step for washing any unbound sample.

The present invention provides a method for the diagnosis of acute neuroborreliosis by the detection of exposure to antigens of *Borrelia burgdorferi*, in any sample, including the steps of: contacting the sample with a peptide microarray comprising at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof under conditions sufficient for any antibodies to *Borrelia burgdorferi* in the sample and the peptides to bind; and visualizing and or quantifying any bound antibody or antibodies to the peptides. The method may optionally include a step for washing any unbound sample.

Any method of detection discussed herein or known in the art can be used for visualizing and/or quantifying the bound antibodies.

Kits

The invention also includes reagents and kits for practicing the methods of the invention. These reagents and kits may vary.

One reagent of the kit would be a peptide or peptides which are reactive with, and specific for antibodies to tick-borne pathogens, comprising: at least one peptide comprising any one of the amino acid sequences in SEQ ID NOs: 1-19 and 29-43 and 60-97 as well as fragments and variants thereof (e.g., SEQ ID NOs: 98-110); or a collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof.

A further embodiment of the kit would include peptide or peptides which are reactive with, and specific for antibodies to tick-borne pathogens, comprising: at least one peptide comprising SEQ ID NOs: 1, 2, 11, 15, 30, 31, 43, 60, 73, 80, and 95-110; or a collection or set of peptides comprising amino acid sequences shifted one residue across at least one peptide comprising any one of the amino acid sequences in SEQ ID NOs: 1, 2, 11, 15, 30, 31, 43, 60, 73, 80, and 95-110; or combinations thereof.

In certain embodiments, the peptides are attached to or immobilized on a solid support. In some embodiments, the peptides are attached to or immobilized on a solid support through a metallic nanolayer (e.g., cadmium, zinc, mercury, gold, silver, copper, or platinum nanolayer). In certain embodiments, the solid support is a bead (e.g., a colloidal particle or a metallic nanoparticle or nanoshell), a flow path in a lateral flow immunoassay device, a flow path in an analytical or centrifugal rotor, a tube or a well (e.g., in a plate), or a sensor (e.g., an electrochemical, optical, or opto-electronic sensor).

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical or centrifugal rotor, a Western blot, a dot blot, a slot blot, or an electrochemical, optical, or opto-electronic sensor.

One further reagent of the kit would be peptide microarrays comprising a peptide or peptides which are reactive with, and specific for antibodies to tick-borne pathogens, comprising: at least one peptide comprising any one of the amino acid sequences in SEQ ID NOs: 1-19 and 29-43 and 60-97 as well as fragments and variants thereof (e.g., SEQ ID NOs: 98-110); or a collection or set of peptides comprising amino acid sequences shifted one residue across at least one peptide comprising any one of the amino acid sequences in SEQ ID NOs: 1-19 and 29-43 and 60-97 as well as fragments and variants thereof (e.g., SEQ ID NOs: 98-110); or combinations thereof.

Further kits could include a peptide or peptides which are reactive with, and specific for antibodies to *Borrelia burgdorferi*, comprising: at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof.

One further reagent of this kit would be peptide microarrays comprising a peptide or peptides which are reactive with, and specific for antibodies to *Borrelia burgdorferi*, comprising: at least one peptide comprising any one of the amino acid sequences in SEQ ID NOs: 1, 2, 4, 7, 8, and 20-28; or a collection or set of peptides comprising amino acid sequences shifted one residue across at least one peptide comprising any one of the amino acid sequences in SEQ ID NOs: 1, 2, 4, 7, 8, and 20-28; or combinations thereof.

Other reagents in the kits could include reagents for preparing the sample, binding any antibodies in the sample with the peptides, washing any unbound sample, visualizing any bound antibody or antibodies, and quantifying any bound antibody or antibodies.

In addition, the kits can include various diluents and buffers, labeled conjugates or other agents for the detection of specifically bound antigens or antibodies (e.g., labeling reagents), and other signal-generating reagents, such as enzyme substrates, cofactors and chromogens. In some embodiments, the kit comprises an anti-human IgG/IgM antibody conjugated to a detectable label (e.g., a metallic nanoparticle, metallic nanoshell, metallic nanolayer, fluorophore, colored latex particle, or enzyme) as a labeling reagent. In other embodiments, the kit comprises protein A, protein G, protein A/G fusion proteins, protein L, or combinations thereof conjugated to a detectable label (e.g., a metallic nanoparticle, metallic nanoshell, metallic nanolayer, fluorophore, colored latex particle, or enzyme) as a labeling reagent. In still other embodiments, the labeling reagents of the kit are a second collection or set of peptides of the invention conjugated to a detectable label (e.g., a metallic nanoparticle, metallic nanoshell, metallic nanolayer, fluorophore, colored latex particle, or enzyme). The second collection or set of peptides can be the same as or different than the collection or set of peptides, which may optionally be attached to or immobilized upon a solid support.

Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, monoclonal antibody detector antibodies, an anti-mouse, anti-dog, anti-cat, anti-chicken, or anti-human antibody conjugated to a detectable label, indicator charts for colorimetric comparisons, disposable gloves, decontamination instructions, applicator sticks or containers, a sample preparatory cup and buffers or other reagents appropriate for constituting a reaction medium allowing the formation of a peptide-antibody complex.

Such kits provide a convenient, efficient way for a clinical laboratory to detect exposure to, and to diagnose infection by a tick-borne pathogen. Thus, in certain embodiments, the kits further comprise instructions.

EXAMPLES

The present invention may be better understood by reference to the following non-limiting examples, which are presented in order to more fully illustrate the preferred embodiments of the invention. They should in no way be construed to limit the broad scope of the invention.

Example 1—Generation of 12-Mer Peptides from Tick-Borne Agents or Pathogens

The array platform employed for the assay can accommodate up to 3 million 12-mer linear peptides. The array slide can be divided into 12 subarrays, each containing approximately 170,000 12-mer peptides. Because peptides are programmed for synthesis in situ, the array composition can be continuously and inexpensively modified based on performance or the need to address new immunological targets.

This platform was used to develop the assay of the invention that targeted 8 principal tick-borne pathogens present in the United States, including *Anaplasma phagocytophilum* (agent of human granulocytic anaplasmosis), *Babesia microti* (babesiosis), *Borrelia burgdorferi* (Lyme disease), *Borrelia miyamotoi, Ehrlichia chaffeensis* (human monocytic ehrlichiosis), *Rickettsia rickettsii* (Rocky Mountain spotted fever), Heartland virus and Powassan virus. A Long Island tick rhabdovirus, a novel virus identified by the inventors in *Amblyomma americanum* ticks through metagenomic sequencing, was also included (Tokarz et al. 2014). See Table 2

The use of 12-mers reflects three considerations: 1) principal and contextual determinants in antibody recognition of linear epitopes; 2) platform constraints; and 3) preliminary data obtained in experiments with spotted peptide arrays.

Principal and Contextual Determinants in Antibody Recognition of Linear Epitopes:

Serum antibodies bind linear peptide sequences ranging from 5 and 9 amino acids (Buus et al. 2012) and bind most efficiently when targets are flanked by additional amino acids.

Platform Constraints:

The current production version of the platform accommodates up to 3 million 5-18 amino acid peptides. Fidelity of synthesis exceeds 99% for 12-mers; costs increase dramatically and fidelity drops significantly beyond this length.

Preliminary Data.

Experiments performed with spotted 12-mer peptides confirmed that people recently vaccinated against influenza, measles, mumps and rubella had serum antibodies that could be detected by cognate peptides on spotted arrays (Robinson et al. 2002). Therefore a 12 mer peptide can display a single linear epitope recognized by serum antibodies.

A database of overlapping 12-mer peptides that tiled the proteome of each of these agents was established. For each antigen selected, all available protein sequences from the NCBI protein database were downloaded. Sequences were clustered and used as a scaffold for the design of 12-mer linear peptides that tiled each protein sequence with 11 amino acid overlap in a sliding window pattern. Redundant 12-mers were excluded prior to synthesis. For viral agents, 12-mer peptides were designed that tiled the entire proteome (Table 2). For non-viral agents, antigen selection was more selective, and based on the current understanding of the triggers of humoral immunity for each agent.

For *B. burgdorferi,* 62 proteins (including paralogs) were selected that are known to elicit an antibody response in humans (Xu et al. 2008; Barbour et al. 2008).

For *B. miyamotoi*, serological diagnosis is typically performed using the glycerophosphodiester phosphodiesterase, as this antigen is present in *B. miyamotoi* infection but not *B. burgdorferi* (Jahfari et al. 2014; Krause et al. 2014; Schwan et al. 1996). The recent availability of the genome sequence of *B. miyamotoi* allowed the investigation of the utility of variable major proteins (VMPs) in serodiagnosis (Barbour 2016). Multiple differentially expressed VMPs have been shown to be antigenic in humans, with variable small protein 1, in particular, being highly immunogenic in the early stage of infection (Wagemakers et al. 2016).

The *B. microti* genome contains one species-specific multi-gene family (bmn) that codes for antigenic surface proteins, which has been shown to be a reliable tool for *B. microti* detection (Lodes et al. 2000; Masatani et al. 2013; Cornillot et al. 2016; Houghton et al. 2002).

*Anaplasma phagocytophilum* major surface proteins (MSPs) have been implicated as the primary diagnostic antigens for anaplasmosis (Krbkova et al. 2016).

For both *E. chaffeensis* and *R. rickettsii*, surface proteins historically used for antibody detection were selected (Gong et al. 2014; Yu et al. 1999).

For each antigen every genetic variant for the 12-mer design was included. For *B. burgdorferi* OspC alone, 12-mer peptides for 25 distinct OspC types was designed. The final design of the array consisted of 169,205 peptides (Table 2).

The unique peptide sequences (169,205+random control peptides) were printed on Roche-NimbleGen arrays using manufacturer instructions. This platform consists of a 75 mm×26 mm array slide divided into 12 subarrays that can accommodate 172,000 peptides per slide allowing a 12 sample query at a cost of less than $200/sample.

TABLE 2

Agents, Antigens and Number of Peptides Used in Assay

| Agent and antigens | Number of 12-mer peptides |
|---|---|
| *Anaplasma phagocytophilum*<br>MSP2, MSP4, MSP5, P55, P62, Omp1N | 16,787 |
| *Babesia microti*<br>SA-1, BMN1 (-2, -3, -4 -5 -6, -7, -8, -10, -11, -12 -13, -17, -20, -21), GPI 12, AMA1; Hsp70, DnaK, Bmp32 | 11,333 |
| *Borrelia burgdorferi*<br>OspA, OspB, OspC, OspD, VlsE, DbpA and B, BmpA-BmpD, P100, OppA, OppA2, RevA, P66, LA7, BBK07, BBK32, BBK50, FlaA, FlaB, FliL, FlgE, DnaK, BBA04, BBA36, BBA57, BBA64, BBA65, BBA66, BBA68, BBA69, BBA73, BBA74, BBI38, BBI42, BBE31, OspE, OspF, Erp (all paralogs), Mlp (all paralogs), Bdr (all paralogs), BBO03 (all paralogs) | 91,338 |
| *Borrelia miyamotoi*<br>GlpQ, FhbA, ipA, P66, OppA2, FlgG, FlaB, FliL, VLP (1, A1, A2, C1, C2, C3, D1, D2, D3, D4, D5, D5S, D6S, D6, D7S, D8, D9, D10, 3S, A2S, 4S 15/16, 18), VSP (1, 2, 3, 4, 6) | 23,946 |

TABLE 2-continued

Agents, Antigens and Number of Peptides Used in Assay

| Agent and antigens | Number of 12-mer peptides |
|---|---|
| *Ehrlichia chaffeensis* | 4,156 |
| P156, P120, P28/omp-1, Gp47, VLPT, SP-related protein | |
| *Rickettsia rickettsii* | 5,855 |
| OmpA, OmpB, OmpW, Porin 4, adr1, adr2 | |
| Heartland virus | 4,153 |
| N, Gn, Gc, L | |
| Powassan virus | 7,688 |
| polyprotein | |
| Long Island tick rhabdovirus | 3,949 |
| N, P, M, G, L | |

Example 2—Further Materials and Methods for Examples 3-7

To test the utility of peptides and peptide microarrays of Example 1 (the TBD-Serochip), well-characterized sera and cerebrospinal fluid (CSF) containing antibodies to one or more agents of TBDs including *A. phagocytophilum, B. burgdorferi, B. microti, E. chaffeensis*, and Powassan virus was used (Table 3). To determine the optimal serum dilution, 16 sera at dilutions of 1:50 and 1:200 and two sera at dilutions of 1:20, 1:50, and 1:200 were tested. The 1:50 serum dilution was determined to be optimal for the TBD-Serochip as the 1:200 dilution did not achieve the required sensitivity in early disease samples and the 1:20 dilution generated adverse signal to noise ratio. A 1:5 dilution was used for CSF.

Figure 1B:
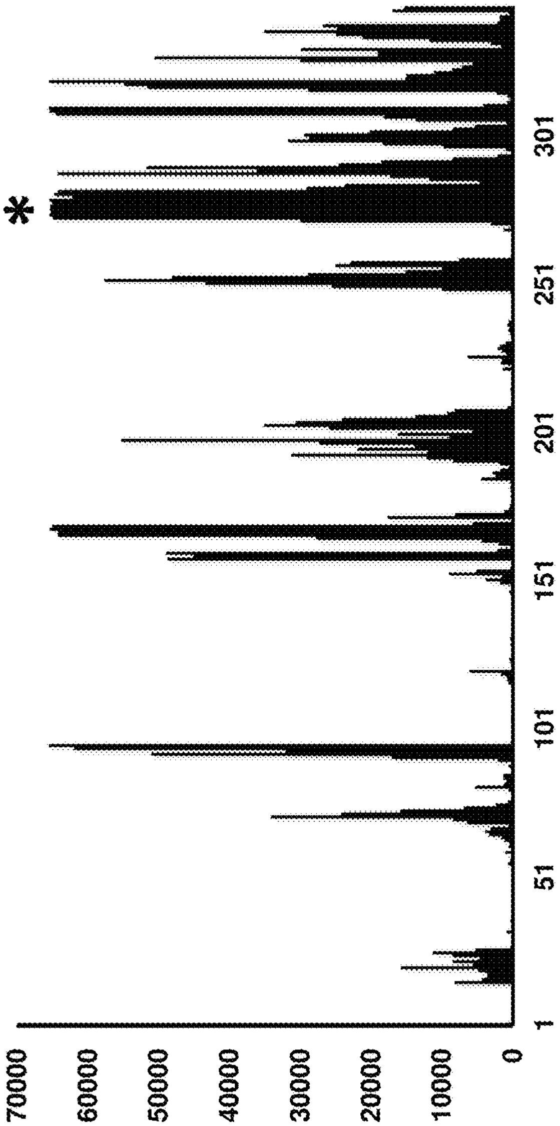
FIG. 1B shows the reactivity data generated for the C6 region of the *B. burgdorferi* VlsE antigen using patient sera from acute neuroborreliosis. The X-axis in each Figure represents the amino acid span of VlsE (mapped to accession number CAJ41626). The Y-axis in each Figure represents the intensity of the fluorescent signal. The asterisk specifies the location of the 12-mer peptides that make up the major immunoreactive region of the C6 peptide of the VlsE protein of *B. burgdorferi*, shown in FIG. 1A.
Figure 2B:
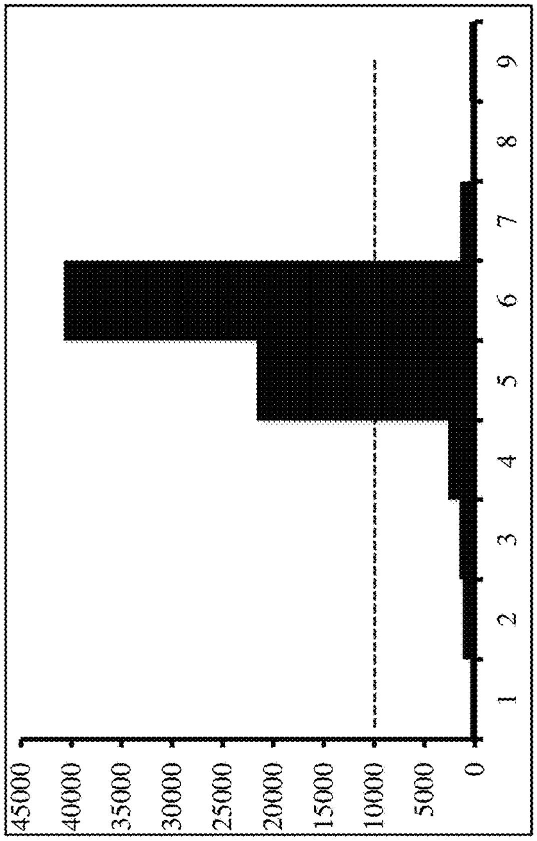
FIGS. 2A and 2B represent results from an early acute LD serum tested twice with the same peptide assay.
Figure 2A:
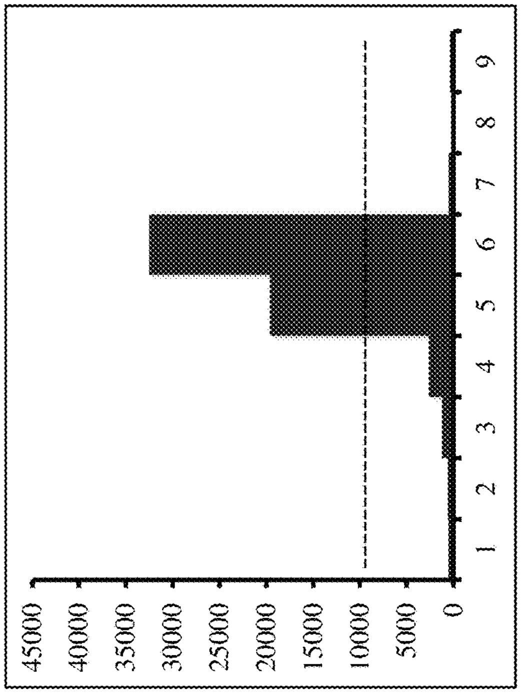
Figures 2C, 2D:
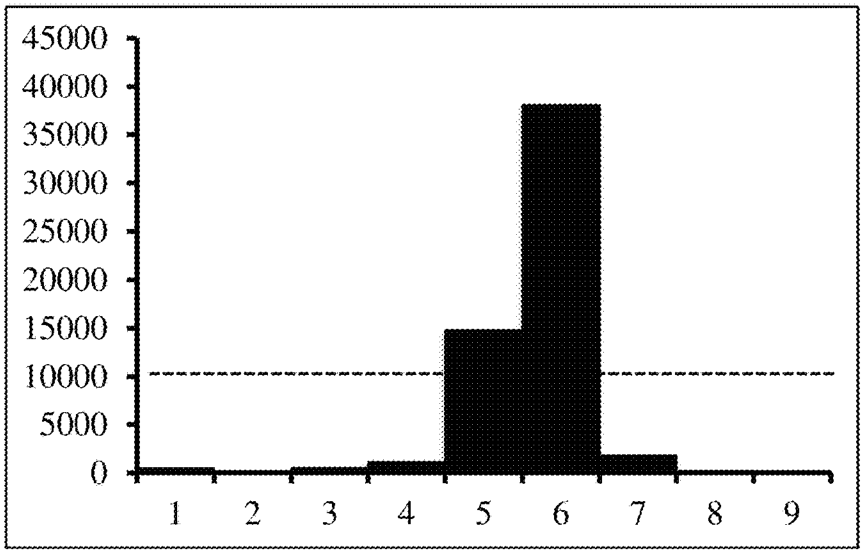
FIG. 2C shows the results from the same sample run on a different peptide assay. The Y-axis in FIGS. 2A-2C represents the intensity of the fluorescence signal, and the X-axis represents a sequence of 9 overlapping peptides within the C6 of the VlsE protein of *B. burgdorferi*.
FIG. 2D shows the sequence of the 9 overlapping peptides within the C6 of the VlsE protein of *B. burgdorferi*. Significant immunoreactive peptides are numbered 5 and 6. Dashed lines in FIGS. 2A-2C represent the threshold for the MKKDDQIAAAIALRGMA (SEQ ID NO: 1) epitope.

For each agent-positive sample examined, all immunoreactive linear epitopes were catalogued (FIG. 1). To assess reproducibility, three sera were tested in duplicate on the same array, and 3 sera on different arrays. The data were highly reproducible with minimal intra- and interchip variation (FIG. 2). Reactive 12-mer peptides displayed 85%-100% signal intensities relative to background when serum samples were tested on the same or different arrays. The immunoreactivity of these epitopes was contrasted with that of controls (consisting of TBD-negative samples and samples with other TBDs). Any identified epitope that was non-reactive within the control group was considered agent-specific. The focus was on identification of epitopes that employed in concert would enhance diagnostic sensitivity and specificity of early disease. Thus, all agent-specific epitopes were characterized and sorted by signal intensity, reproducibility, and their utility for diagnosis of disease stage.

Human Samples

De-identified human sera and cerebral spinal fluid (CSF) samples were acquired from the New York State Department of Health, State University of New York at Stony Brook, the Lyme and Tick-Borne Disease Research Center at Columbia University, Long Island University, National Institutes of Health and the Centers for Disease Control and Prevention. Sample types ranged from early and late Lyme disease (confirmed by the two-tiered testing algorithm), non-Lyme TBDs (babesiosis, anaplasmosis, ehrlichiosis and Powassan disease), and Lyme ELISA-negative controls. All anaplasmosis and babesiosis samples were retested at the Center for Infection and Immunity by IFA (Fuller Labs, Ca) prior to the TBD-Serochip analysis. For selected Lyme disease-positive sera, the C6 ELISA (Gold Standard Diagnostics) was performed according to manufacturer's instructions (at a dilution of 1:20). Paired sera and cerebrospinal fluid samples from patients with acute Lyme neuroborreliosis were obtained under a clinical protocol (ClinicalTrials.gov Identifier: NCT00028080) approved by the institutional review board of the National Institute of Allergy and Infectious Diseases, and all patients signed informed consent.

Data Acquisition and Analysis

Samples were diluted in binding buffer (0.1M Tris-Cl, 1% alkali soluble casein, 0.05% Tween-20) and hybridized to the arrays at 4° C. for 14 hours. Arrays were washed 3 times for 10 minutes each on Little Dipper (SciGene) with 1×TBST (0.05% Tween-20) at room temperature. Secondary antibodies were diluted in binding buffer at concentration of 1 ug/ml. Secondary antibody incubation was done in Plastic Coplin Jar (Fisher Scientific) for 3 hours at room temperature with gentle agitation. To enable simultaneous detection of both IgM and IgG antibodies, a secondary antibody incubation method was used where Alexa Fluor 647-AffiniPure Goat Anti-Human IgG, Fcy fragment specific (Jackson ImmunoResearch Labs, Inc) was first bound to the array, then washed 3 times (10 minutes each) on Little Dipper with 1×TBST at room temperature and spun dry. This was followed by binding Cy3-conjugated AffiniPure Fab fragment Goat Anti-Human IgM, Fc5μ Fragment (Jackson ImmunoResearch Labs, Inc), repeating the same washing and drying methods. The slides were scanned on NimbleGen MS 200 Microarray Scanner (Roche) at 2 μm resolution, with an excitation wavelength of 532 nm for Cy3/IgM and 635 nm for Alexa Flour/IgG respectively. The relative fluorescent unit (RFU) signals for all the probes were extracted from the images using Roche Sequencing Solutions image extraction software. The RFU signals were converted into intensity plots after quantile normalization, background and spatial correction, and deconvolution for redundant peptides. To determine background noise, signal intensity data for each antigen was obtained from 26 control serum and 20 cerebrospinal fluids (CSF) samples found to be negative for all agents tested. A reactive epitope was identified by a continuous set of overlapping 12-mer peptides with signal intensities above threshold in samples with known TBDs. The signal threshold was defined for each reactive epitope by calculating the mean plus 3 standard deviations of the signal intensity for the same epitope in the 26 negative control samples. An epitope was considered reactive when the signal intensity for at least two contiguous 12-mer peptides was above threshold. An individual sample was called positive when reactive with at least one specific epitope.

TABLE 3

Samples Tested in Examples 2-7

| Disease | Sample type | Number of samples tested |
|---|---|---|
| Lyme disease | serum | 36 |
| Lyme disease-neuroborreliosis | serum | 10 |
| Lyme disease-neuroborreliosis | CSF | 10 |
| Lyme disease and babesiosis | serum | 10 |
| Babesiosis | serum | 6 |
| Anaplasmosis | serum | 7 |
| *Borrelia miyamotoi* disease | serum | 7 |
| Powassan virus disease | serum | 6 |
| Ehlichiosis | serum | 1 |
| CDC validation set | serum | 32 |
| Southern tick associated rash illness | serum | 10 |
| Southern tick associated rash illness | CSF | 10 |

TABLE 3-continued

| Samples Tested in Examples 2-7 | | |
|---|---|---|
| Disease | Sample type | Number of samples tested |
| Lyme disease negative | serum | 15 |
| Healthy controls | serum | 20 |
| Negative control-polyomavirus | serum | 2 |
| Total samples | | 182 |

Example 3—Utility of Peptides and Assay to Detect Antibodies of TBD Pathogens or Agents Using Lyme Disease Samples Sixty-six samples from patients with Lyme disease (Tables 3, 4 and 5) were tested. These included 27 sera from early acute Lyme disease (western blot IgM positive, western blot IgG negative or indeterminate), 19 western blot IgG positive sera, and 10 paired sera and CSF from patients diagnosed with acute neuroborreliosis. Ten of these samples (7 early, 3 disseminated) previously also tested positive for antibody to *B. microti*. For controls, 15 sera submitted for Lyme disease testing that were negative by the two-tiered testing algorithm, two sera from patients with a chronic polyomavirus infection, and 10 paired sera and CSF from patients diagnosed with southern tick associated rash illness, a tick-borne syndrome of unknown etiology (Masters et al. 2008).

The analysis resulted in the identification of over 100 reactive epitopes including 13 that were most useful for diagnosis of early Lyme disease (Tables 1, 4 and 5). VlsE was the most prominent antigen in both early and disseminated disease with multiple reactive epitopes identified throughout this lipoprotein (FIG. 1, Table 5).

The most consistently reactive epitope was a 17 amino acid portion of the well-characterized immunodominant C6 region (Bacon et al. 2003; Liang et al. 1999). This epitope was reactive in every IgG positive Lyme serum tested and in 16 out of 27 of early Lyme disease samples.

Other frequently reactive epitopes in early Lyme disease were located within FlaB, OspC, BmpA, DbpA, and BBK07 (Table 1).

Although highly reactive in Lyme disease patients, the extensive cross-reactivity of FlaB makes it unsuitable as a diagnostic antigen (Luft et al. 1993). The 13 amino acid peptide fragment identified by the TBD-Serochip excludes other cross-reactive epitopes and highlights its diagnostic utility.

The OspC Nt epitope along with epitopes located within variable OspC regions were useful for detection of IgM in early disease. In sera where reactivity to these epitopes was not detected, reactivity to epitopes on other antigens was used for diagnosis, including previously unrecognized epitopes on P100, OppA, Bdr, and paralogs of BBO03, a cp32-encoded lipoprotein. This panel of 13 epitopes was also useful for diagnosis of IgG positive samples (Tables 5 and 6).

TABLE 4

| Early Lyme disease samples | | | | | | | | | | | | | | | | | | |
|---|---|---|---|---|---|---|---|---|---|---|---|---|---|---|---|---|---|---|
| Sample | WB IgM | # of WB IgM bands | WB IgG | # of WB IgG bands | C6 index CII | VlsE | FlaB | OspCNt | OspC type K | OspC type M | P100 | BBK07 | Bdr | OppA | BmpA | Dbp -1 | Dbp -2 | BBO03 |
| RTS-900 | POS | 2 | NEG | 0 | .34 | | | | | | | | | + | | | | |
| RTS-901 | POS | 2 | NEG | 0 | 1.38 | | | | | | | + | + | + | + | | + | |
| RTS-902 | POS | 3 | NEG | 0 | 7.78 | + | | | | | | + | | | | + | | |
| RTS-903 | POS | 3 | NEG | 1 | 7.39 | + | + | | | | | | | | | | | |
| RTS-904 | POS | 2 | NEG | 1 | 1.3 | | + | | + | | | | | | + | | | |
| RTS-905 | POS | 2 | NEG | 1 | 1.15 | | | | | | | | | + | | | | |
| RTS-906 | POS | 2 | NEG | 1 | 0.25 | | | | | | | | | | | | | + |
| RTS-907 | POS | 2 | NEG | 1 | 8.2 | + | | | | | | | | | | | | |
| RTS-908 | POS | 2 | NEG | 1 | 1.4 | + | | | | | | | | | + | | | |
| RTS-909 | POS | 2 | NEG | 2 | 1.51 | + | + | + | | | | | | | | | | |
| RTS-910 | POS | 2 | NEG | 2 | 3.61 | + | | | | | | + | | | | | + | |
| RTS-911 | POS | 2 | NEG | 3 | N.D. | + | | | | | | + | + | | | | | |
| RTS-912 | POS | 2 | NEG | 4 | 2.38 | + | | | | | | + | | | + | | | |
| RTS-201 | POS | na | NEG | na | ND | + | + | | | | | | | | | | | |
| RTS-600 | POS | na | NEG | na | ND | + | + | | + | | | + | | + | | | | |
| RTS-602 | POS | na | NEG | na | 0.61 | | | | | | | | + | | | | | |
| RTS-604 | NEG | na | NEG | na | .39 | | | | | | | + | | | | | | |

TABLE 4-continued

| Early Lyme disease samples | | | | | | | | | | | | | | | | | | |
|---|---|---|---|---|---|---|---|---|---|---|---|---|---|---|---|---|---|---|
| Sample | WB IgM | # of WB IgM bands | WB IgG | # of WB IgG bands | C6 index CII | VlsE | FlaB | OspCNt | OspC type K | OspC type M | P100 | BBK07 | Bdr | OppA | BmpA | Dbp -1 | Dbp -2 | BBO03 |
| RTS-606 | POS | na | NEG | na | ND | | | | | | + | | | | | | | + |
| RTS-607 | POS | na | NEG | na | ND | + | | | | | | | | | + | | | |
| RTS-609 | POS | na | NEG | na | ND | + | | | | | | | | | | | | |
| RTS-614 | POS | na | NEG | na | .99 | | | + | | | + | | | | | | | |
| RTS-615 | POS | na | NEG | na | ND | | | | + | | | | | | | | | |
| RTS-619 | POS | na | NEG | na | 4.8 | | | | | | | + | | | | | | + |
| RTS-620 | POS | na | NEG | na | 2.97 | + | | + | + | | | | | | + | + | | |
| RTS-625 | POS | na | NEG | na | ND | + | | | | | | | | | | | | |
| RTS-628 | POS | na | NEG | na | ND | + | | | | | | | | | | | | |
| RTS-633 | POS | na | NEG | na | ND | + | | + | | | | | | | | | | |

na data not available;
NEG negative;
ND not done;
+ indicates TBD-Serochip signal intensity above threshold

TABLE 5

| IgG Positive Lyme Disease Samples | | | | | | | | | | | | | | | | | | |
|---|---|---|---|---|---|---|---|---|---|---|---|---|---|---|---|---|---|---|
| Sample | WB IgM | # of WB IgM | WB IgG | # of WB IgG | C6 index CII | VlsE | FlaB | OspCNt | OspC type K | OspC Type M | P100 | BBK07 | Bdr | OppA | BmpA | DbpA-1 | DbpA-2 | BBO03 |
| RTS-913 | IND | 1 | POS | 6 | 4.68 | + | | | | | | + | | | + | | | |
| RTS-914 | NEG | | POS | 6 | 4.8 | + | | | | | | | | | + | | + | |
| RTS-915 | NEG | | POS | 7 | ND | + | + | | | | | + | | | | | | |
| RTS-916 | IND | 1 | POS | 7 | ND | + | | | | | | | | | + | | | |
| RTS-0202 | NEG | na | POS | na | ND | + | + | | + | | | | | | | + | | |
| RTS-0204 | POS | na | POS | na | ND | + | + | | | | | | | | | | | |
| RTS-0205 | POS | na | POS | na | ND | + | | | | + | | | | | + | | | |
| RTS-0206 | POS | na | POS | na | ND | + | + | | | | | + | | | | | | + |
| RTS-0207 | POS | na | POS | na | ND | + | + | | | | | + | | | | + | + | |
| RTS-0208 | POS | na | POS | na | ND | + | + | | + | | | | | | | + | | |
| RTS-0209 | POS | na | POS | na | ND | + | + | | | | | + | | | | | | |
| RTS-0210 | POS | na | POS | na | ND | + | + | | | | | + | | | + | | | + |
| RTS-0211 | POS | na | POS | na | ND | + | + | | | | | + | | | | | | |
| RTS-0212 | POS | na | POS | na | ND | + | + | | | | | + | | | | + | | |
| RTS-0213 | POS | na | POS | na | ND | + | + | | | | | + | | | | | + | |
| RTS-0219 | NEG | na | POS | na | ND | + | + | | | | | | + | | | | | + |

TABLE 5-continued

IgG Positive Lyme Disease Samples

| Sample | WB IgM | # of WB IgM | WB IgG | # of WB IgG | C6 index CII | VlsE | FlaB | OspCNt | OspC type K | OspC Type M | P100 | BBK07 | Bdr | OppA | BmpA | DbpA-1 | DbpA-2 | BBO03 |
|---|---|---|---|---|---|---|---|---|---|---|---|---|---|---|---|---|---|---|
| RTS-0220 | POS | na | POS | na | ND | + | + | | | | | + | | | | + | | |
| RTS-655 | POS | na | POS | na | 10 | + | + | | | | | | | | + | | | + |
| RTS-659 | NEG | na | POS | na | ND | + | + | | + | | | + | | | | | + | |

na data not available;
NEG negative;
ND not done;
+ sign indicates TBD-Serochip signal intensity above threshold

TABLE 6

Most Frequently Reactive IgG Epitopes in Samples from Patients with Acute Neuroborreliosis

| | | NB1 | | NB2 | | NB3 | | NB4 | | NB5 | |
|---|---|---|---|---|---|---|---|---|---|---|---|
| Antigen | Peptide | CSF | Serum | CSF | Serum | CSF | Serum | CSF | Serum | CSF | Serum |
| VlsE | (SEQ ID NO. 1) | + | + | + | + | + | + | + | + | + | + |
| | (SEQ ID NO. 20) | + | + | + | + | + | + | + | + | | |
| | (SEQ ID NO. 21) | | | | | + | + | + | + | | |
| BBK07 | (SEQ ID NO. 7) | + | + | | + | + | + | + | + | + | + |
| FlaB | (SEQ ID NO. 2) | + | + | | | | | + | + | + | + |
| OspC | (SEQ ID NO. 4) | | + | | | | | | + | | + |
| | (SEQ ID NO. 22 | | + | | | | | + | + | | |
| Bdr* | (SEQ ID NO. 8) | + | + | | + | | | + | + | + | + |
| BBO03^ | (SEQ ID NO. 23) | + | + | | | | | + | + | + | + |
| DbpA | (SEQ ID NO. 24) | | + | | + | | | | | + | + |
| BBK32 | (SEQ ID NO. 25) | | + | | + | | + | | + | | + |
| BBI38 | (SEQ ID NO. 26) | + | + | | + | | | | | + | + |
| OspE | (SEQ ID NO. 27) | | + | | + | | | | + | | + |
| P37 | (SEQ ID NO. 28) | | | + | + | + | | | | + | + |

| | | NB6 | | NB7 | | NB8 | | NB9 | | NB10 | |
|---|---|---|---|---|---|---|---|---|---|---|---|
| Antigen | Peptide | CSF | Serum | CSF | Serum | CSF | Serum | CSF | Serum | CSF | Serum |
| VlsE | (SEQ ID NO. 1) | + | + | + | + | + | + | + | + | + | + |
| | (SEQ ID NO. 20) | | | | | | + | | | + | + |
| | (SEQ ID NO. 21) | + | + | + | + | | + | + | + | | |
| BBK07 | (SEQ ID NO. 7) | | + | + | + | | + | + | + | | |
| FlaB | (SEQ ID NO. 2) | + | + | + | + | + | + | + | + | | |
| OspC | (SEQ ID NO. 4) | | | | | | | | | + | + |
| | (SEQ ID NO. 22) | | + | | + | | | | + | | |
| Bdr* | (SEQ ID NO. 8) | | | | | | | | + | + | + |
| BBO03^ | (SEQ ID NO. 23) | + | + | | | | + | | | | |
| DbpA | (SEQ ID NO. 24) | + | + | | | | + | | | | |
| BBK32 | (SEQ ID NO. 25) | | | | | | + | | + | | |
| BBI38 | (SEQ ID NO. 26) | | | | | | | | | + | + |
| OspE | (SEQ ID NO. 27) | | + | | | | | | | + | + |
| P37 | (SEQ ID NO. 28) | | | | | | | | | | |

+ indicates signal intensity on the serochip;
NB# represents individual patient with neuroborreliosis;
*Cp-32-encoded Bdr paralog family;
^Cp-32 encoded representative of paralog DUF228 family

Figure 3A:
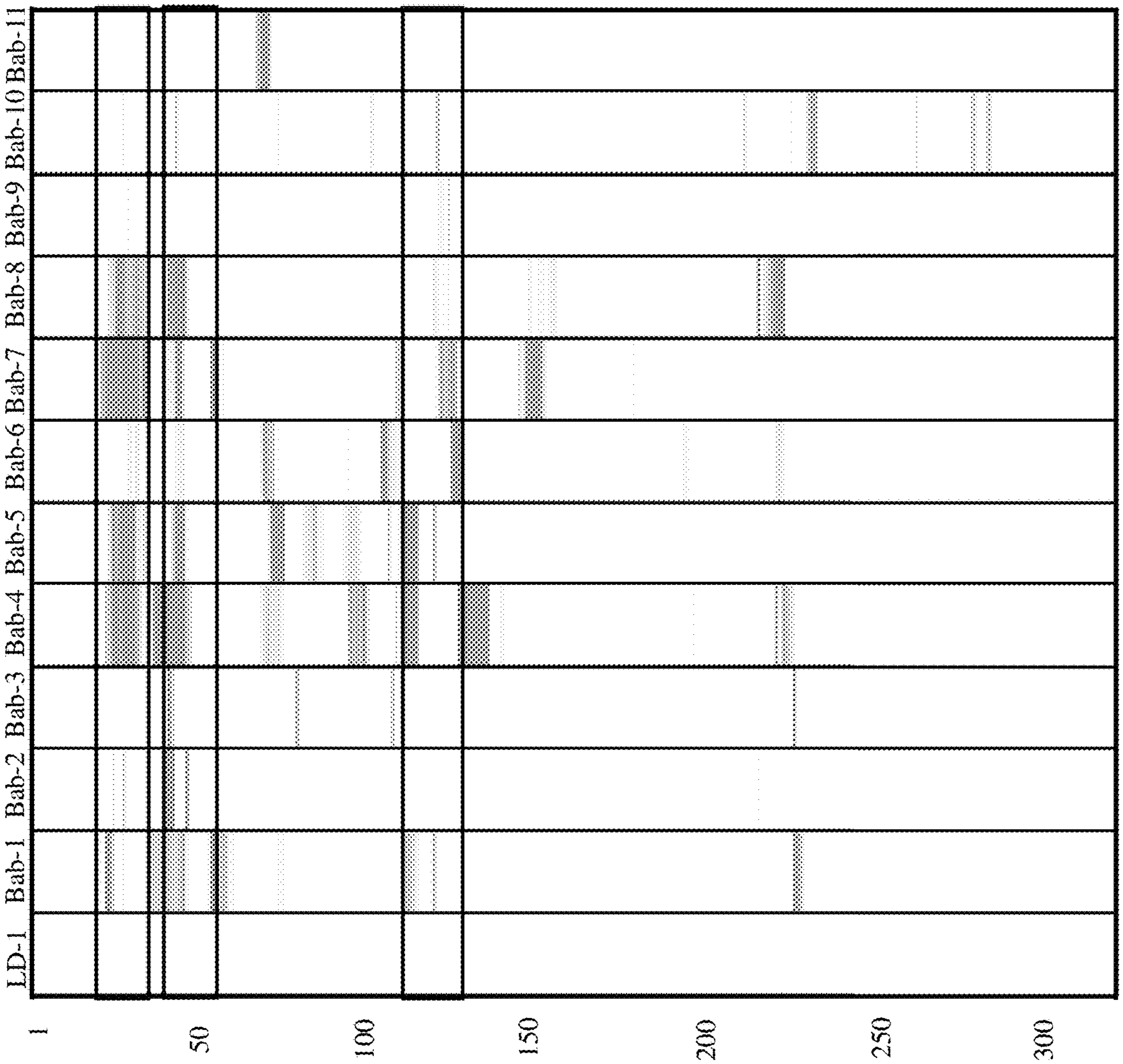
FIG. 3A is a heatmap for SA-1 antigens and FIG. 3B is a heatmap for BMN 1-17 antigens. The numbers on the Y-axis represent the location of 12-mer peptides positioned along the continuous protein sequence of each antigen. The X-axis are the samples. Bab-1 to Bab-11 represent *B. microti*-antibody positive sera, and LD-1 represents Lyme disease positive serum. Immunoreactivity with the 12-mer peptide is indicated in gray with increasing signal intensity displayed from light to dark. The dark brackets across the map indicates the range of discriminatory peptides from Table 1.
Figure 3B:
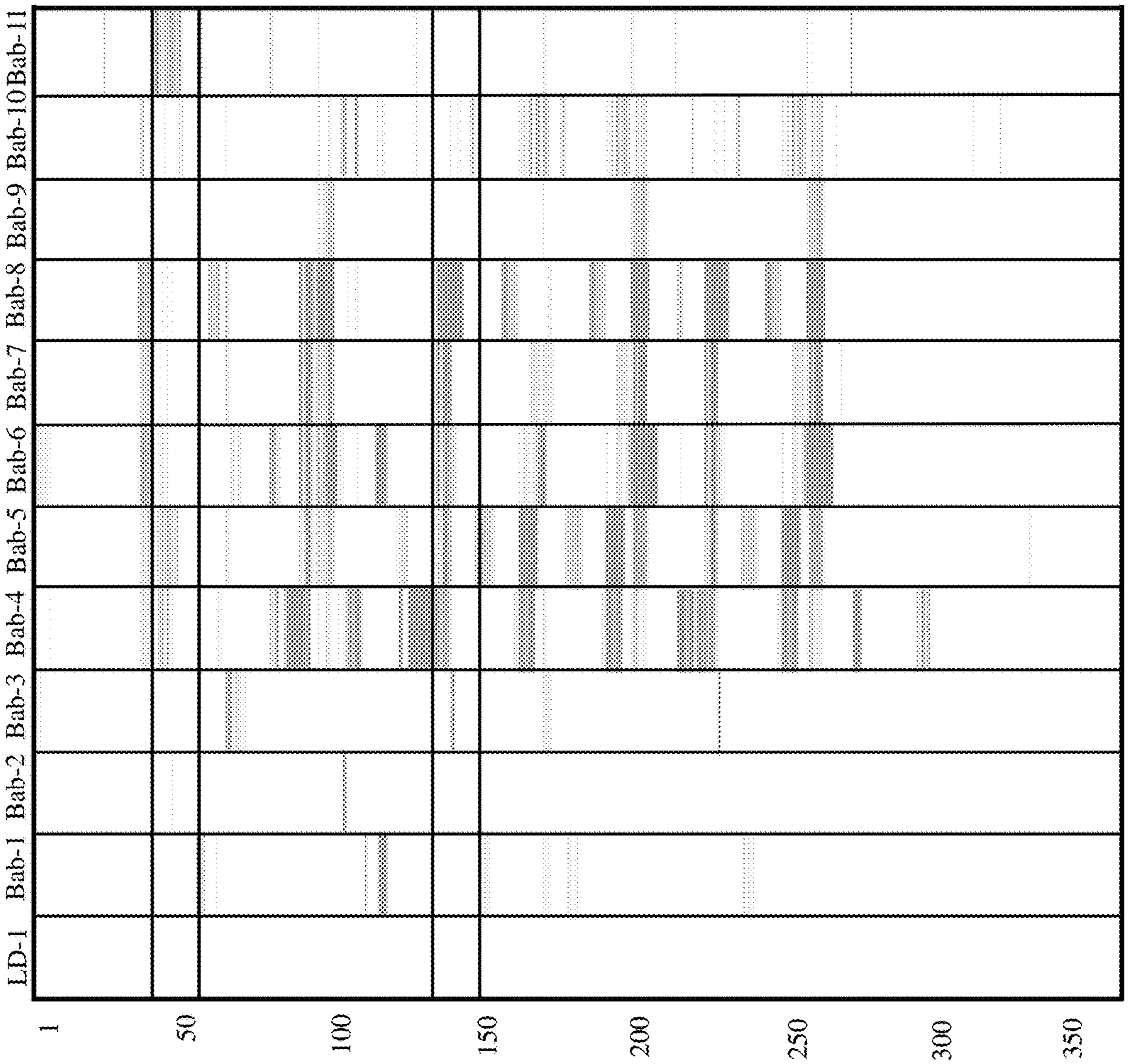

Example 4—Utility of Peptides and Assay to Detect Antibodies of TBD Pathogens or Agents Using Babesiosis Samples Sixteen *B. microti*-antibody positive sera were tested and six unique frequently reactive specific epitopes (three within SA-1, five within BMN 1-17, and one on BMN 1-3) were identified (Table 1, FIG. 3). Ten of these sera also previously tested positive for *B. burgdorferi* by the two-tiered testing algorithm and all ten were positive for *B. burgdorferi* by the TBD-Serochip, displaying the utility of this platform for simultaneous detection of concurrent or past infections with more than one agent. In the remaining 46 Lyme disease positive and 15 Lyme-negative sera, *B. microti* antibodies were detected in 4 out of 46 Lyme disease sera (9%), and in 1 out of 15 Lyme negative sera. None of these samples were previously tested for babesiosis.

Figure 4:
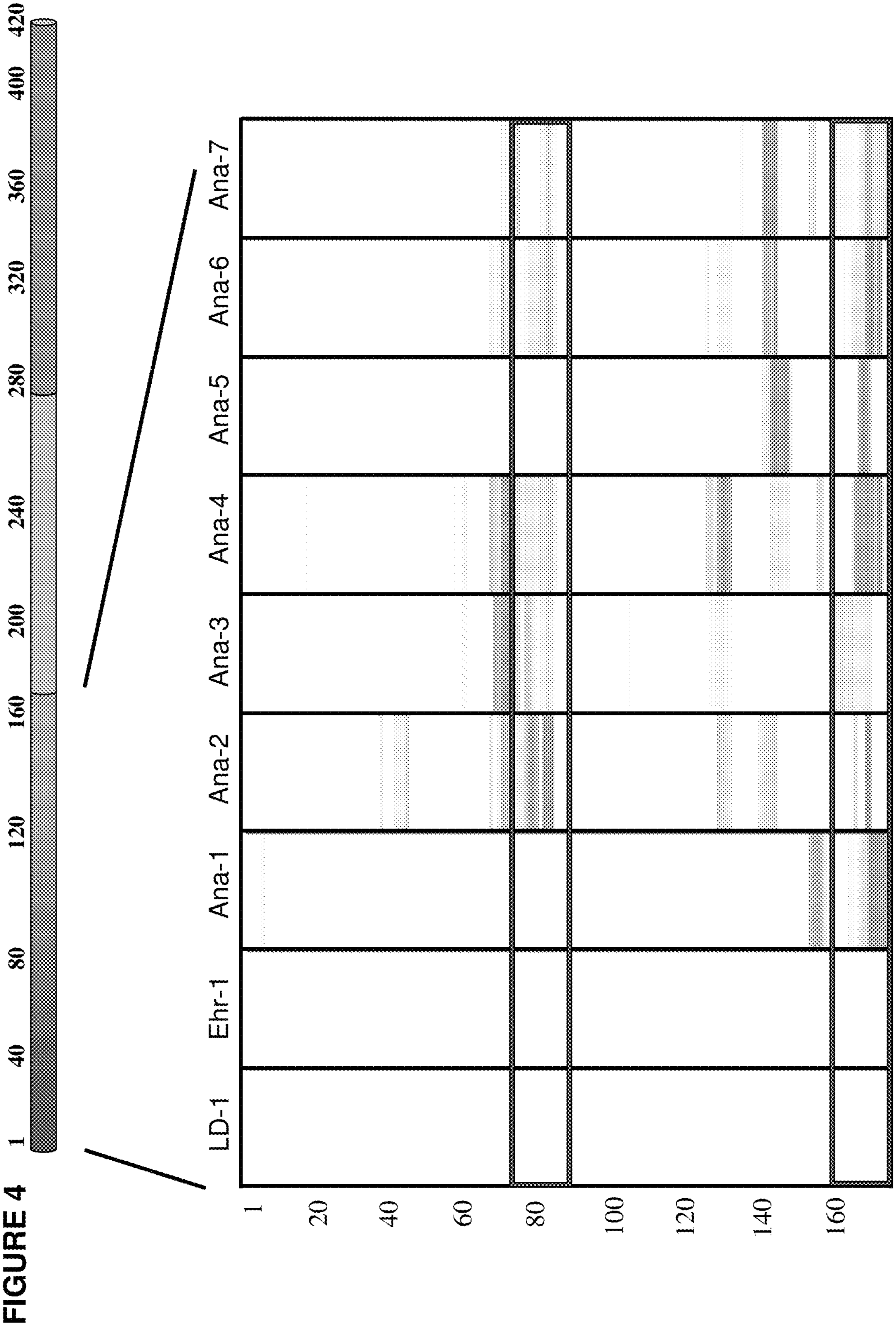
FIG. 4 shows the discovery of *A. phagocytophilum*-specific epitopes on MSP2. A schematic of the MSP2 antigen (accession number WP 044108210) indicating the approximate lengths of the conserved N and C fragments flanking the central variable core is shown on top. The heatmap displays in gray the immunoreactivity of the 176 amino acid N-terminal region, with increasing signal intensity displayed from light to dark. The numbers on the Y-axis represent the location of 12-mer peptides positioned along the contiguous sequence of the N terminal region. The X-axis are the samples. Ana-1 to Ana-7 indicate anaplasmosis-positive sera, LD-1 and Ehr-1 indicate Lyme disease and ehlichiosis sera, respectively. The dark brackets indicate the location of the discriminatory epitopes from Table 1.

Example 5—Utility of Peptides and Assay to Detect Antibodies of TBD Pathogens or Agents Using Anaplasmosis Samples Sera from seven patients diagnosed with anaplasmosis were tested. Highly reactive peptides on major surface protein 2 (MSP2, also referred to as P44) were identified. Peptides from MS3-MS5 had limited reactivity and no diagnostic utility in the assay. MSP2 consists of conserved N and C termini surrounding a highly variable central core. All seven samples were reactive with multiple epitopes within the N terminus, with epitope TSGKDIVQFAKAVEIS (SEQ ID NO: 18) flanking the variable region reactive in every sample tested (FIG. 4). The reactivity was specific to *A. phagocytophilum*, and no reactivity was detected when sera from a patient with an *E. chaffeensis* infection, a tick-transmitted pathogen that frequently cross-reacts in tests for anaplasmosis, was tested. In addition, five of these seven samples had antibodies to another TBD-agent, with three sera positive for *B. burgdorferi* and two for *B. microti*. Four out of 56 Lyme disease sera were also reactive to these *A. phagocytophilum* specific epitopes.

Figure 5:
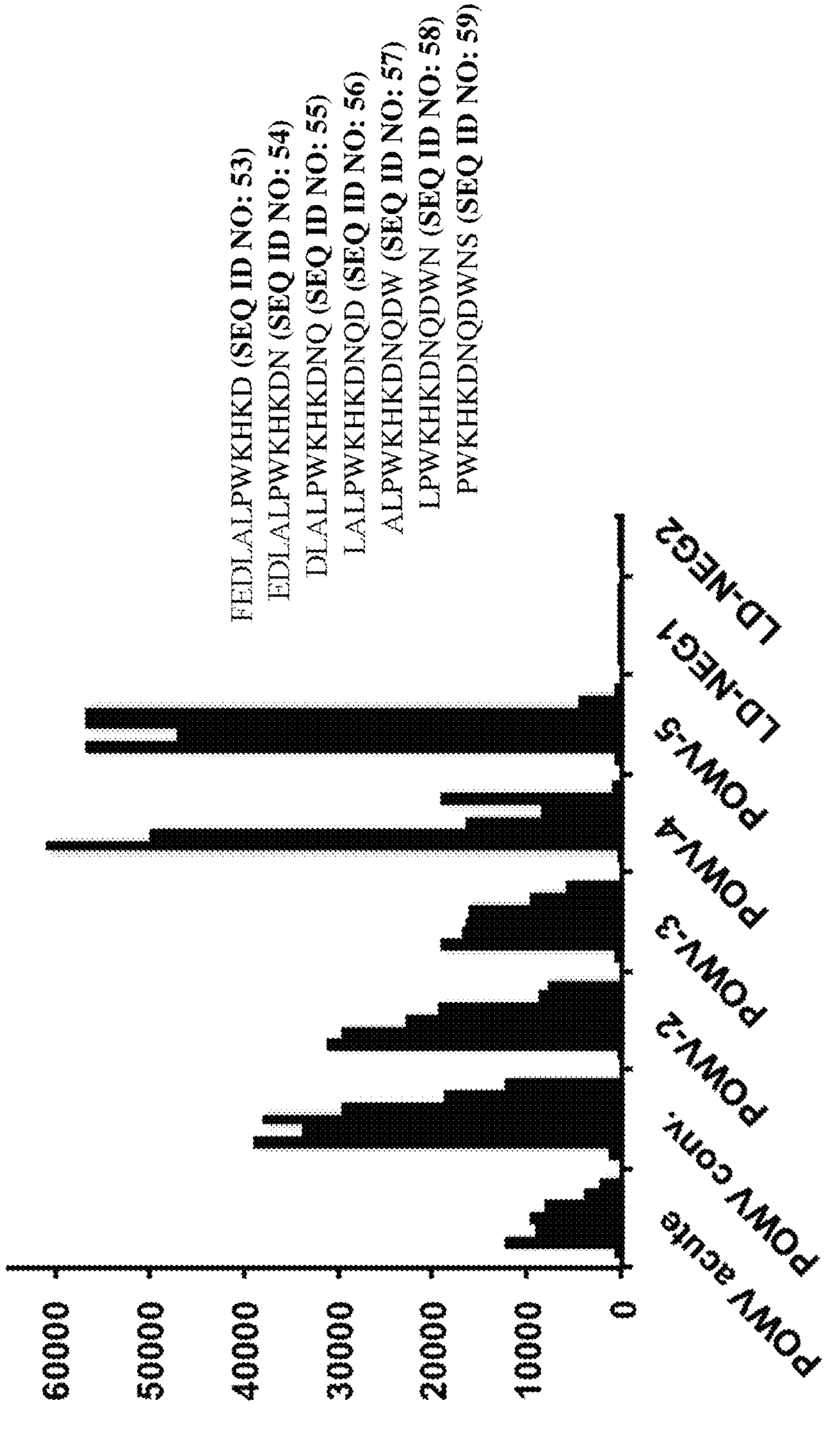
FIG. 5 shows the identification of a POWV-specific peptide using the peptide array. The Y-axis represents the intensity of the fluorescence signal for the seven peptides to the right. The bottom six peptides in the Figure are the reactive 12-mer peptides. The X-axis represents the samples. POWV indicate Powassan virus positive samples and LD-NEG corresponds to negative control samples.

Example 6—Utility of Peptides and Assay to Detect Antibodies of TBD Pathogens or Agents Using Samples Positive for Powassan Virus Six POWV-positive samples were tested, consisting of four convalescent sera and paired acute and convalescent sera. All samples reacted with a specific epitope within the glycoprotein of lineage II of POWV (deer-tick virus) (FIG. 5). Three of the 56 Lyme disease sera, none with a reported history of POWV infection, had reactivity to this epitope.

Example 7—Utility of Peptides and Assays to Detect Antibodies of TBD Pathogens or Agents Using Samples Positive for *Babesia Microti*

Seven convalescent sera from patients with a confirmed infection with *B. miyamotoi* were tested. Nine reactive epitopes on FlaB, Vsp and Vlp antigens were selected that in concert detected *B. miyamotoi* (BMD) and differentiate it from Lyme disease.

Example 8—Utility of Peptides and Assay to Detect Antibodies of TBD Pathogens or Agents Using a CDC Validation Set A set of 32 samples available from the CDC that are used for validation of novel diagnostic platforms were tested (Molins et al. 2014). This set (Research I panel) contained both Lyme disease positive sera (early acute with erythema migrans, disseminated, and late disease) and LD-negative sera (healthy residents of LD-endemic and non-endemic regions) controls and persons who have no history of LD but have other diseases (infectious mononucleosis, fibromyalgia, multiple sclerosis, rheumatoid arthritis, syphilis and severe periodontitis) that may cause serologic cross-reactivity in antibody-based tests for LD. The analysis of these samples indicated that the TBD-Serochip offers improvement relative to the two-tiered algorithm for the identification of early Lyme disease (Table 7). In addition, the results of this analysis allowed the further streamlining of the list of key epitopes into the panel shown in Table 1.

TABLE 7

Reactivity of discriminatory epitopes for *B. burgdorferi* on the Lyme disease positive sera from the CDC Research panel I

| Sample Category | Sample Group | Acute/ Convalescent | EIA | IgM WB | IgM WB bands | IgG | IgG WB Bands | 2-Tier Interpretation |
|---|---|---|---|---|---|---|---|---|
| Lyme disease | Early Lyme-EM 1 | Acute | Neg | Neg | — | Neg | 1 | Neg |
| Lyme disease | Early Lyme-EM 2 | Acute | Neg | Neg | — | Neg | 1 | Neg |
| Lyme disease | Early Lyme-EM 3 | Acute | Neg | Neg | — | Neg | 2 | Neg |
| Lyme disease | Early Lyme-EM 4 | Acute | Neg | Pos | 2 | Neg | 2 | Neg |
| Lyme disease | Early Lyme-EM 5 | Convalescent | Pos | Pos | 2 | Neg | 2 | Pos |
| Lyme disease | Early Lyme-EM 6 | Convalescent | Pos | Pos | 2 | Neg | 4 | Pos |
| Lyme disease | Early Lyme-EM 7 | Convalescent | Pos | Pos | 2 | Pos | 5 | Pos |
| Lyme disease | Early Lyme-EM 8 | Convalescent | Pos | Pos | 3 | Neg | 3 | Pos |
| Lyme disease | Neurologic Lyme 9 | — | Pos | Pos | 3 | Pos | 5 | Pos |
| Lyme disease | Neurologic Lyme 10 | — | Pos | Pos | 2 | Pos | 10 | Pos |
| Lyme disease | Lyme arthritis 11 | — | Pos | Neg | 1 | Pos | 7 | Pos |
| Lyme disease | Lyme arthritis 12 | — | Pos | Neg | 1 | Pos | 10 | Pos |

| Sample Group | VlsE | FlaB | OspCNt | OspC type K | OspC type M | P100 | BBK07 | Bdr | OppA | BmpA | DbpA-1 | DbpA-2 | BBO03 |
|---|---|---|---|---|---|---|---|---|---|---|---|---|---|
| Early Lyme-EM 1 | + | | | | | | | | | | | | |
| Early Lyme-EM 2 | | | | | | | | | | | | | + |
| Early Lyme-EM 3 | + | | | | | | | | | | | | |
| Early Lyme-EM 4 | | | + | | | + | | | + | | | | + |
| Early Lyme-EM 5 | + | + | | | | | + | | + | | | | |
| Early Lyme-EM 6 | + | | | | + | | | | | | | | + |
| Early Lyme-EM 7 | + | | | + | | | | | + | + | | | |
| Early Lyme-EM 8 | + | | + | | | + | | | | + | + | + | |
| Neurologic Lyme 9 | + | + | + | | | + | | | | | | | |

TABLE 7-continued

Reactivity of discriminatory epitopes for *B. burgdorferi* on the Lyme disease positive sera from the CDC Research panel I

| | | | | | | | |
|---|---|---|---|---|---|---|---|
| Neurologic Lyme 10 | + | + | | + | + | + | + |
| Lyme arthritis 11 | + | + | + | + | | + | + |
| Lyme arthritis 12 | + | + | | + | | | |

+ indicates TBD-Serochip signal intensity above threshold

REFERENCES

Adams, et al. Summary of Notifiable Infectious Diseases and Conditions—United States, 2013. *Morb. Mortal Wkly. Rep.* 2015 62:1-122.

Adrion, et al. Health care costs, utilization and patterns of care following Lyme disease. *PLoS One* 2015 10:e0116767.

Aguero-Rosenfeld, et al. Diagnosis of Lyme Borreliosis. *Clin. Microbiol. Rev.* 2005 18:484-509.

Aliota, et al. The prevalence of zoonotic tick-borne pathogens in *Ixodes scapularis* collected in the Hudson Valley, New York State. *Vector Borne Zoonotic Dis.* 2014 14:245-50.

Anderson et al. *J. Immunol. Methods* 2011 366:79-88.

Ang, et al. Large differences between test strategies for the detection of anti-*Borrelia* antibodies are revealed by comparing eight ELISAs and five immunoblots. *Eur. J. Clin. Microbiol. Infect. Dis.* 2011 30:1027-32.

Bacon, et al. Serodiagnosis of Lyme disease by kinetic enzyme-linked immunosorbent assay using recombinant VlsE1 or peptide antigens of *Borrelia burgdorferi* compared with 2-tiered testing using whole-cell lysates. *J. Infect. Dis.* 2003 187:1187-99.

Barbour, Multiple and Diverse vsp and vlp Sequences in *Borrelia miyamotoi*, a Hard Tick-Borne Zoonotic Pathogen. *PLoS One* 2016 11:e0146283.

Barbour, et al. A genome-wide proteome array reveals a limited set of immunogens in natural infections of humans and white-footed mice with *Borrelia burgdorferi*. *Infect. Immun.* 2008 76:3374-89.

Biggs, et al. Diagnosis and Management of Tickborne Rickettsial Diseases: Rocky Mountain Spotted Fever and Other Spotted Fever Group Rickettsioses, Ehrlichioses, and Anaplasmosis—United States. *MMWR Recomm. Rep.* 2016 65:1-44.

Buus, et al. High-resolution mapping of linear antibody epitopes using ultrahigh-density peptide microarrays. *Mol. Cell. Proteomics* 2012 11:1790-800.

Centers for Disease Control, Prevention. Recommendations for test performance and interpretation from the Second National Conference on Serologic Diagnosis of Lyme Disease. *Morb. Mortal. Wkly. Rep.* 1995 44:590-1.

Connally, et al. Testing practices and volume of non-Lyme tickborne diseases in the United States. *Tick Borne Dis.* 2016 7:193-8.

Cornillot, et al. A targeted immunomic approach identifies diagnostic antigens in the human pathogen *Babesia microti*. *Transfusion* 2016.

Curcio, et al. Seroprevalence of *Babesia microti* in Individuals with Lyme Disease. *Vector Borne Zoonotic Dis.* 2016 16:737-43.

Fallon, et al. A comparison of Lyme disease serologic test results from four laboratories in patients with persistent symptoms after antibiotic treatment. *Clin. Infect. Dis.* 2014 59:1705-10.

Gong, et al. Identification of novel surface-exposed proteins of *Rickettsia rickettsii* by affinity purification and proteomics. *PLoS One* 2014 9:e100253.

Hinckley, et al. Lyme disease testing by large commercial laboratories in the United States. *Clin. Infect. Dis.* 2014 59:676-81.

Houghton, et al. Identification of *Babesia microti*-specific immunodominant epitopes and development of a peptide EIA for detection of antibodies in serum. *Transfusion* 2002 42:1488-96.

Jahfari, et al. High seroprevalence of *Borrelia miyamotoi* antibodies in forestry workers and individuals suspected of human granulocytic anaplasmosis in the Netherlands. *New Microbes New Infect.* 2014 2:144-9.

Khatchikian, et al. Recent and rapid population growth and range expansion of the Lyme disease tick vector, *Ixodes scapularis*, in North America. *Evolution* 2015 69:1678-89.

Krause, et al. *Borrelia miyamotoi* sensu lato seroreactivity and seroprevalence in the northeastern United States. *Emerg Infect. Dis.* 2014 20:1183-90.

Kosoy, et al. Novel thogotovirus associated with febrile illness and death, United States, 2014. *Emerg Infect Dis* 2015; 21:760-4.

Krbkova, et al. Assessment of antibodies against surface and outer membrane proteins of *Anaplasma phagocytophilum* in Lyme borreliosis and tick-borne encephalitis paediatric patients. *Epidemiol. Infect.* 2016 144:2597-604.

Kugeler, et al. Geographic Distribution and Expansion of Human Lyme Disease, United States. *Emerg. Infect. Dis.* 2015 21:1455-7.

Liang, et al. Sensitive and specific serodiagnosis of Lyme disease by enzyme-linked immunosorbent assay with a peptide based on an immunodominant conserved region of *Borrelia burgdorferi* vlsE. *J. Clin. Microbiol.* 1999 37:3990-6.

Lodes, et al. Serological expression cloning of novel immunoreactive antigens of *Babesia microti*. *Infect, Immun,* 2000 68:2783-90.

Luft, et al. Cross-reactive antigenic domains of the flagellin protein of *Borrelia burgdorferi*. *Res. Microbiol.* 1993 144:251-7.

Masatani, et al. Identification, cloning and characterization of BmP41, a common antigenic protein of *Babesia microti*. *J. Vet, Med, Sci,* 2013 75:967-70.

Masters, et al. STARI, or Masters disease: Lone Star tick-vectored Lyme-like illness. *Infect. Dis. Clin. North Am.* 2008 22:361-76

Molins, et al. Collection and characterization of samples for establishment of a serum repository for Lyme disease diagnostic test development and evaluation. *J. Clin. Microbiol.* 2014 52:3755-62.

Nelder, et al. Human pathogens associated with the black-legged tick *Ixodes scapularis*: a systematic review. *Parasit. Vectors* 2016 9:265.

Nelson, et al. Incidence of Clinician-Diagnosed Lyme Disease, United States, 2005-2010. *Emerging Infect. Dis.* 2015 21:1625-31.

Pastula, et al. Notes from the field: Heartland virus disease—United States, 2012-2013. *Morb. Mortal. Wkly. Rep.* 2014 63:270-1.

Piantadosi, et al. Emerging Cases of Powassan Virus Encephalitis in New England: Clinical Presentation, Imaging, and Review of the Literature. *Clin. Infect. Dis.* 2016 62:707-13.

Porwancher, et al. Multiplex immunoassay for Lyme disease using VlsE1-IgG and pepC10-IgM antibodies: improving test performance through bioinformatics. *Clin. Vaccine Immunol.* 2011 18:851-9.

Robinson, et al. *Nat. Med.* 2002 8:295-301.

Schwan, et al. GlpQ: an antigen for serological discrimination between relapsing fever and Lyme borreliosis. *J. Clin. Microbiol.* 1996 34:2483-92.

Seriburi, et al. High frequency of false positive IgM immunoblots for *Borrelia burgdorferi* in clinical practice. *Clin. Microbiol. Infect.* 2012 18:1236-40.

Signorino et al. Identification of OppA2 linear epitopes as serodiagnostic markers for Lyme disease. *Clin Vaccine Immunol* 2014; 21:704-11.

Stromdahl, et al. Beyond Lyme: aetiology of tick-borne human diseases with emphasis on the south-eastern United States. *Zoonoses Public Health* 2012 59 Suppl 2:48-64.

Theel The Past, Present, and (Possible) Future of Serologic Testing for Lyme Disease. *J. Clin. Microbiol.* 2016; 54:1191-6.

Tokarz, et al. Detection of *Anaplasma phagocytophilum, Babesia microti, Borrelia burgdorferi, Borrelia miyamotoi*, and Powassan Virus in Ticks by a Multiplex Real-Time Reverse Transcription-PCR Assay. *mSphere* 2017 2.

Tokarz, et al. Genome characterization of Long Island tick rhabdovirus, a new virus identified in *Amblyomma americanum* ticks. *Virol. J.* 2014 11:26.

Tokarz, et al. Assessment of polymicrobial infections in ticks in New York state. *Vector Borne Zoonotic Dis.* 2010 10:217-21.

Tokarz, et al. Combined effects of blood and temperature shift on *Borrelia burgdorferi* gene expression as determined by whole genome DNA array. *Infect. Immun.* 2004 72:5419-32. Vigil, et al. *Future Microbiol.* 2010 5:241-51.

Wagemakers et al. Variable Major Proteins as Targets for Specific Antibodies against *Borrelia miyamotoi. J. Immunol.* 2016 196:4185-95.

White, et al. Lyme Disease Surveillance in New York State: an Assessment of Case Underreporting. *Zoonoses Public Health* 2016.

Wormser, et al. Single-tier testing with the C6 peptide ELISA kit compared with two-tier testing for Lyme disease. *Diagn. Microbiol. Infect. Dis.* 2013 75:9-15.

Xu, et al. Profiling the humoral immune response to *Borrelia burgdorferi* infection with protein microarrays. *Microb. Pathog.* 2008 45:403-7.

Yu, et al. Comparison of *Ehrlichia chaffeensis* recombinant proteins for serologic diagnosis of human monocytotropic ehrlichiosis. *J. Clin. Microbiol.* 1999 37:2568-75.

The invention claimed is:

1. A lateral flow immunoassay device, or a peptide microarray, having thereon three or more isolated peptides, each peptide reactive with and specific for antibodies to a tick-borne pathogen, the three or more isolated peptides comprising:

(i) a first peptide consisting of the amino acid sequence of SEQ ID NO: 1, or a 12 amino acid fragment thereof consisting of SEQ ID NO: 47 or SEQ ID NO: 48;

(ii) a second peptide consisting of the amino acid sequence of SEQ ID NO: 11, or SEQ ID NO: 15; and (iii) a third peptide consisting of the amino acid sequence of SEQ ID NO: 18, or SEQ ID NO:95.

2. The lateral flow immunoassay device or peptide microarray of claim 1, further comprising an additional peptide consisting of the amino acid sequence of SEQ ID NO:2.

3. The lateral flow immunoassay device or peptide microarray of claim 1 for differential serological detection of exposure to, and/or infection by, a tick-borne pathogen, wherein the second peptide consists of the amino acid sequence of SEQ ID NO: 11.

4. The lateral flow immunoassay device or peptide microarray of claim 1 for differential serological detection of exposure to, and/or infection by, a tick-borne pathogen, a wherein the second peptide consists of the amino acid sequence of SEQ ID NO: 15.

5. The lateral flow immunoassay device of claim 1, wherein each peptide is on a flow path in the lateral flow immunoassay device.

6. The lateral flow immunoassay device of claim 5, wherein the flow path comprises a porous membrane.

7. The lateral flow immunoassay device of claim 6, wherein the porous membrane comprises nitrocellulose or polyvinylidene fluoride.

8. The lateral flow immunoassay device of claim 1, wherein the peptides are attached to or immobilized on a solid support of the lateral flow immunoassay device.

9. The lateral flow immunoassay device of claim 1, comprising a reporter that labels human antibodies.

10. The lateral flow immunoassay device of claim 9, wherein the reporter that labels human antibodies comprises colloidal gold.

11. The lateral flow immunoassay device of claim 1, wherein the peptides are conjugated to a ligand and complexed with labeled ligand receptor.

12. The lateral flow immunoassay device of claim 11, wherein the ligand comprises biotin.

13. The lateral flow immunoassay device of claim 11, wherein the labeled ligand receptor comprises streptavidin-colloidal gold.

14. The lateral flow immunoassay device or peptide microarray of claim 1, wherein the third peptide consists of the amino acid sequence of SEQ ID NO: 18.

15. The lateral flow immunoassay device or peptide microarray of claim 1, a wherein the third peptide consists of the amino acid sequence of SEQ ID NO: 95.

16. The lateral flow immunoassay device or peptide microarray of claim 1, wherein the first peptide consists of the amino acid sequence of SEQ ID NO: 47 or SEQ ID NO: 48.

17. A method for the differential serological detection of exposure to, and/or infection by, a tick-borne pathogen which causes Lyme disease, anaplasmosis or babesiosis in a subject, comprising:

a) contacting the lateral flow immunoassay device or peptide microarray of claim 1 with a sample from the subject under conditions sufficient to allow the binding of the antibodies to the peptide(s); and b) visualizing any antibody or antibodies bound to the peptide(s), so as to thereby identify a tick-borne pathogen in the sample which causes Lyme disease, anaplasmosis or babesiosis, wherein antibodies that bind to SEQ ID NO: 1 indicate Lyme disease, antibodies that bind to SEQ ID NO: 18 or SEQ ID NO: 95 indicate anaplasmosis, and antibodies that bind to SEQ ID NO:11 or SEQ ID NO:15 indicate babesiosis.

18. The method of claim 17, wherein the subject has been previously diagnosed with a tick-borne disease.

* * * * *

SEQUENCE LISTING

```
<160> NUMBER OF SEQ ID NOS: 110

<210> SEQ ID NO 1
<211> LENGTH: 17
<212> TYPE: PRT
<213> ORGANISM: Borrelia burgdorferi

<400> SEQUENCE: 1

Met Lys Lys Asp Asp Gln Ile Ala Ala Ala Ile Ala Leu Arg Gly Met
1               5                   10                  15

Ala


<210> SEQ ID NO 2
<211> LENGTH: 13
<212> TYPE: PRT
<213> ORGANISM: Borrelia burgdorferi

<400> SEQUENCE: 2

Val Gln Glu Gly Val Gln Gln Glu Gly Ala Gln Gln Pro
1               5                   10


<210> SEQ ID NO 3
<211> LENGTH: 13
<212> TYPE: PRT
<213> ORGANISM: Borrelia burgdorferi

<400> SEQUENCE: 3

Asn Ser Gly Lys Asp Gly Asn Thr Ser Ala Asn Ser Ala
1               5                   10
```

<210> SEQ ID NO 4
<211> LENGTH: 13
<212> TYPE: PRT
<213> ORGANISM: Borrelia burgdorferi

<400> SEQUENCE: 4

Lys Ala Ile Leu Thr Thr Asp Ala Ala Lys Asp Lys Gly
1 5 10

<210> SEQ ID NO 5
<211> LENGTH: 13
<212> TYPE: PRT
<213> ORGANISM: Borrelia burgdorferi

<400> SEQUENCE: 5

Ala Ala Ile Leu Lys Thr Asn Gly Thr Lys Asp Lys Gly
1 5 10

<210> SEQ ID NO 6
<211> LENGTH: 16
<212> TYPE: PRT
<213> ORGANISM: Borrelia burgdorferi

<400> SEQUENCE: 6

Ser Asp Ile Asp Ile Asp Ser Leu Val Thr Asp Lys Val Val Ala Ala
1 5 10 15

<210> SEQ ID NO 7
<211> LENGTH: 17
<212> TYPE: PRT
<213> ORGANISM: Borrelia burgdorferi

<400> SEQUENCE: 7

Ser Glu Lys Ile Thr Lys Leu Thr Pro Glu Glu Leu Glu Asn Leu Ala
1 5 10 15

Lys

<210> SEQ ID NO 8
<211> LENGTH: 14
<212> TYPE: PRT
<213> ORGANISM: Borrelia burgdorferi

<400> SEQUENCE: 8

Asp Leu Glu Asn Leu Glu Lys Gln Phe Asp Ile Lys Phe Asp
1 5 10

<210> SEQ ID NO 9
<211> LENGTH: 14
<212> TYPE: PRT
<213> ORGANISM: Borrelia burgdorferi

<400> SEQUENCE: 9

Val Ala Tyr Asn Met Tyr Ile Asn Gly Glu Leu Asp Phe Leu
1 5 10

<210> SEQ ID NO 10
<211> LENGTH: 16
<212> TYPE: PRT
<213> ORGANISM: Borrelia burgdorferi

<400> SEQUENCE: 10

Lys Phe Asp Lys Leu Glu Asn His Pro Phe Leu Gly Tyr Pro Tyr Lys
1 5 10 15

<210> SEQ ID NO 11
<211> LENGTH: 14
<212> TYPE: PRT
<213> ORGANISM: Babesia microti

<400> SEQUENCE: 11

Val Leu Ser Ala Gly Gly Ser Gly Gly Asn Gly Gly Asn Gly
1 5 10

<210> SEQ ID NO 12
<211> LENGTH: 15
<212> TYPE: PRT
<213> ORGANISM: Babesia microti

<400> SEQUENCE: 12

His Gln Glu Gln Asn Asn Ala Asn Asp Ser Ser Asn Pro Thr Gly
1 5 10 15

<210> SEQ ID NO 13
<211> LENGTH: 16
<212> TYPE: PRT
<213> ORGANISM: Babesia microti

<400> SEQUENCE: 13

Glu Lys Asn Lys Lys Phe Asn Glu Asn Leu Val Lys Ile Glu Lys Arg
1 5 10 15

<210> SEQ ID NO 14
<211> LENGTH: 15
<212> TYPE: PRT
<213> ORGANISM: Babesia microti

<400> SEQUENCE: 14

Gly Glu Asn Asp Ile Ile Gln Pro Pro Trp Glu Asp Thr Ala Pro
1 5 10 15

<210> SEQ ID NO 15
<211> LENGTH: 15
<212> TYPE: PRT
<213> ORGANISM: Babesia microti

<400> SEQUENCE: 15

Asn Lys Ser Glu Lys Ala Glu Arg Lys Ser His Asp Thr Gln Thr
1 5 10 15

<210> SEQ ID NO 16
<211> LENGTH: 16
<212> TYPE: PRT
<213> ORGANISM: Babesia microti

<400> SEQUENCE: 16

Gly Thr Gly Trp Pro Ser Glu Ala Gly Gly Pro Ser Glu Ala Gly Gly
1 5 10 15

<210> SEQ ID NO 17
<211> LENGTH: 17
<212> TYPE: PRT
<213> ORGANISM: Anaplasma phagocytophilum

<400> SEQUENCE: 17

Phe Asp Trp Asn Thr Pro Asp Pro Arg Ile Gly Phe Lys Asp Asn Met
1 5 10 15

Leu

<210> SEQ ID NO 18
<211> LENGTH: 16
<212> TYPE: PRT
<213> ORGANISM: Anaplasma phagocytophilum

<400> SEQUENCE: 18

Thr Ser Gly Lys Asp Ile Val Gln Phe Ala Lys Ala Val Glu Ile Ser
1 5 10 15

<210> SEQ ID NO 19
<211> LENGTH: 16
<212> TYPE: PRT
<213> ORGANISM: Powassan virus

<400> SEQUENCE: 19

Glu Asp Leu Ala Leu Pro Trp Lys His Lys Asp Asn Gln Asp Trp Asn
1 5 10 15

<210> SEQ ID NO 20
<211> LENGTH: 13
<212> TYPE: PRT
<213> ORGANISM: Borrelia burgdorferi

<400> SEQUENCE: 20

Lys Asn Pro Ile Ala Ala Ala Ile Gly Asp Lys Asp Gly
1 5 10

<210> SEQ ID NO 21
<211> LENGTH: 15
<212> TYPE: PRT
<213> ORGANISM: Borrelia burgdorferi

<400> SEQUENCE: 21

Arg Lys Val Leu Gly Ala Ile Thr Gly Leu Ile Gly Asp Ala Val
1 5 10 15

<210> SEQ ID NO 22
<211> LENGTH: 14
<212> TYPE: PRT
<213> ORGANISM: Borrelia burgdorferi

<400> SEQUENCE: 22

Asn Ser Val Lys Glu Leu Thr Ser Pro Val Val Val Glu Ser
1 5 10

<210> SEQ ID NO 23
<211> LENGTH: 18
<212> TYPE: PRT
<213> ORGANISM: Borrelia burgdorferi

<400> SEQUENCE: 23

Gly Ile Thr Lys Ile Lys Glu Glu Phe Asp Lys Lys Val Ala Glu Ile
1 5 10 15

Lys Ala

<210> SEQ ID NO 24
<211> LENGTH: 15
<212> TYPE: PRT
<213> ORGANISM: Borrelia burgdorferi

<400> SEQUENCE: 24

Gly Val Asn Phe Asp Ala Phe Lys Asp Lys Lys Thr Gly Ser Gly
1 5 10 15

<210> SEQ ID NO 25
<211> LENGTH: 18
<212> TYPE: PRT
<213> ORGANISM: Borrelia burgdorferi

<400> SEQUENCE: 25

Glu Met Lys Glu Glu Ser Pro Gly Leu Phe Asp Lys Gly Asn Ser Ile
1 5 10 15

Leu Glu

<210> SEQ ID NO 26
<211> LENGTH: 16
<212> TYPE: PRT
<213> ORGANISM: Borrelia burgdorferi

<400> SEQUENCE: 26

Gln Thr Leu Ser Lys Glu Lys Ala Glu Glu Leu Leu Gln His Ala Glu
1 5 10 15

<210> SEQ ID NO 27
<211> LENGTH: 14
<212> TYPE: PRT
<213> ORGANISM: Borrelia burgdorferi

<400> SEQUENCE: 27

Arg Lys Glu Lys Asp Gly Ile Glu Thr Gly Leu Asn Ala Gly
1 5 10

<210> SEQ ID NO 28
<211> LENGTH: 17
<212> TYPE: PRT
<213> ORGANISM: Borrelia burgdorferi

<400> SEQUENCE: 28

Leu Asn Val Cys Tyr Thr Asp Ala Ile Ala Ala Leu Ala Lys Ala Lys
1 5 10 15

Asn

<210> SEQ ID NO 29
<211> LENGTH: 16
<212> TYPE: PRT
<213> ORGANISM: Borrelia burgdorferi

<400> SEQUENCE: 29

Val Gly Met Thr Phe Arg Ala Gln Glu Gly Ala Phe Leu Thr Gly Tyr
1 5 10 15

<210> SEQ ID NO 30
<211> LENGTH: 15
<212> TYPE: PRT
<213> ORGANISM: Borrelia burgdorferi

<400> SEQUENCE: 30

Asp Ala Phe Lys Asp Lys Lys Thr Gly Ser Gly Val Ser Glu Asn
1 5 10 15

<210> SEQ ID NO 31
<211> LENGTH: 15
<212> TYPE: PRT
<213> ORGANISM: Borrelia burgdorferi

<400> SEQUENCE: 31

-continued

Ala Ala Phe Lys Glu Asp Lys Thr Gly Ser Lys Val Ser Glu Asn
1 5 10 15

<210> SEQ ID NO 32
<211> LENGTH: 19
<212> TYPE: PRT
<213> ORGANISM: Babesia microti

<400> SEQUENCE: 32

Arg Lys Glu Gly His Gly Lys Pro Asn Thr Asn Lys Ser Glu Lys Ala
1 5 10 15

Glu Arg Lys

<210> SEQ ID NO 33
<211> LENGTH: 20
<212> TYPE: PRT
<213> ORGANISM: Babesia microti

<400> SEQUENCE: 33

His Asp Lys Ile Asn Lys Asn Lys Ser Gly Asn Ala Gly Ile Lys Ser
1 5 10 15

Tyr Asp Thr Gln
20

<210> SEQ ID NO 34
<211> LENGTH: 18
<212> TYPE: PRT
<213> ORGANISM: Babesia microti

<400> SEQUENCE: 34

Asn Lys Asn Lys Ser Gly Lys Ala Gly Ile Lys Ser His Asn Thr Gln
1 5 10 15

Thr Pro

<210> SEQ ID NO 35
<211> LENGTH: 15
<212> TYPE: PRT
<213> ORGANISM: Borrelia miyamotoi

<400> SEQUENCE: 35

Lys Lys Ile Lys Asp Ala Val Glu Phe Ala Ala Asn Val Lys Glu
1 5 10 15

<210> SEQ ID NO 36
<211> LENGTH: 17
<212> TYPE: PRT
<213> ORGANISM: Borrelia miyamotoi

<400> SEQUENCE: 36

Gly Cys Asn Asn Gly Gly Gly Glu Asp Pro Gln Lys Phe Leu Thr Ser
1 5 10 15

Ile

<210> SEQ ID NO 37
<211> LENGTH: 21
<212> TYPE: PRT
<213> ORGANISM: Borrelia miyamotoi

<400> SEQUENCE: 37

Ala Glu Thr Lys Lys Glu Asp Ile Gly Lys Tyr Phe Ala Asp Ile Glu
1 5 10 15

Lys Thr Met Thr Leu

20

<210> SEQ ID NO 38
<211> LENGTH: 19
<212> TYPE: PRT
<213> ORGANISM: Borrelia miyamotoi

<400> SEQUENCE: 38

Thr Asp Gly Ile Glu Lys Ala Lys Asp Ala Ala Glu Ile Ala Ile Ala
1 5 10 15

Pro Ala Val

<210> SEQ ID NO 39
<211> LENGTH: 16
<212> TYPE: PRT
<213> ORGANISM: Borrelia miyamotoi

<400> SEQUENCE: 39

Asn Ser Asn Thr Lys Lys Ser Asp Val Gly Val Tyr Phe Lys Lys Val
1 5 10 15

<210> SEQ ID NO 40
<211> LENGTH: 17
<212> TYPE: PRT
<213> ORGANISM: Borrelia miyamotoi

<400> SEQUENCE: 40

Val Thr Gly Ala Asp Ile Leu Gln Ala Ile Val Lys Asp Asn Gly Glu
1 5 10 15

Ala

<210> SEQ ID NO 41
<211> LENGTH: 17
<212> TYPE: PRT
<213> ORGANISM: Borrelia miyamotoi

<400> SEQUENCE: 41

Lys Thr Thr Thr Lys Lys Asn Asp Val Gly Val Tyr Phe Asn Ser Leu
1 5 10 15

Gly

<210> SEQ ID NO 42
<211> LENGTH: 17
<212> TYPE: PRT
<213> ORGANISM: Borrelia miyamotoi

<400> SEQUENCE: 42

Leu Lys Phe Ala Lys Gly Gly Ser Asp Ala His Leu Ser Asn Ser Ala
1 5 10 15

Asn

<210> SEQ ID NO 43
<211> LENGTH: 13
<212> TYPE: PRT
<213> ORGANISM: Borrelia miyamotoi

<400> SEQUENCE: 43

Ala Gln Ala Ala Pro Ala Gln Glu Gly Ala Gln Gln Glu
1 5 10

<210> SEQ ID NO 44
<211> LENGTH: 12

<212> TYPE: PRT
<213> ORGANISM: Borrelia burgdorferi

<400> SEQUENCE: 44

Met Lys Lys Asp Asp Gln Ile Ala Ala Ala Ile Ala
1 5 10

<210> SEQ ID NO 45
<211> LENGTH: 12
<212> TYPE: PRT
<213> ORGANISM: Borrelia burgdorferi

<400> SEQUENCE: 45

Lys Lys Asp Asp Gln Ile Ala Ala Ala Ile Ala Leu
1 5 10

<210> SEQ ID NO 46
<211> LENGTH: 12
<212> TYPE: PRT
<213> ORGANISM: Borrelia burgdorferi

<400> SEQUENCE: 46

Lys Asp Asp Gln Ile Ala Ala Ala Ile Ala Leu Arg
1 5 10

<210> SEQ ID NO 47
<211> LENGTH: 12
<212> TYPE: PRT
<213> ORGANISM: Borrelia burgdorferi

<400> SEQUENCE: 47

Asp Asp Gln Ile Ala Ala Ala Ile Ala Leu Arg Gly
1 5 10

<210> SEQ ID NO 48
<211> LENGTH: 12
<212> TYPE: PRT
<213> ORGANISM: Borrelia burgdorferi

<400> SEQUENCE: 48

Asp Gln Ile Ala Ala Ala Ile Ala Leu Arg Gly Met
1 5 10

<210> SEQ ID NO 49
<211> LENGTH: 12
<212> TYPE: PRT
<213> ORGANISM: Borrelia burgdorferi

<400> SEQUENCE: 49

Gln Ile Ala Ala Ala Ile Ala Leu Arg Gly Met Ala
1 5 10

<210> SEQ ID NO 50
<211> LENGTH: 12
<212> TYPE: PRT
<213> ORGANISM: Borrelia burgdorferi

<400> SEQUENCE: 50

Glu Met Lys Lys Asp Asp Gln Ile Ala Ala Ala Ile
1 5 10

<210> SEQ ID NO 51
<211> LENGTH: 12
<212> TYPE: PRT
<213> ORGANISM: Borrelia burgdorferi

<400> SEQUENCE: 51

Ile Ala Ala Ala Ile Ala Leu Arg Gly Met Ala Lys
1               5                   10

<210> SEQ ID NO 52
<211> LENGTH: 12
<212> TYPE: PRT
<213> ORGANISM: Borrelia burgdorferi

<400> SEQUENCE: 52

Ala Ala Ala Ile Ala Leu Arg Gly Met Ala Lys Asp
1               5                   10

<210> SEQ ID NO 53
<211> LENGTH: 12
<212> TYPE: PRT
<213> ORGANISM: Powassan virus

<400> SEQUENCE: 53

Phe Glu Asp Leu Ala Leu Pro Trp Lys His Lys Asp
1               5                   10

<210> SEQ ID NO 54
<211> LENGTH: 12
<212> TYPE: PRT
<213> ORGANISM: Powassan virus

<400> SEQUENCE: 54

Glu Asp Leu Ala Leu Pro Trp Lys His Lys Asp Asn
1               5                   10

<210> SEQ ID NO 55
<211> LENGTH: 12
<212> TYPE: PRT
<213> ORGANISM: Powassan virus

<400> SEQUENCE: 55

Asp Leu Ala Leu Pro Trp Lys His Lys Asp Asn Gln
1               5                   10

<210> SEQ ID NO 56
<211> LENGTH: 12
<212> TYPE: PRT
<213> ORGANISM: Powassan virus

<400> SEQUENCE: 56

Leu Ala Leu Pro Trp Lys His Lys Asp Asn Gln Asp
1               5                   10

<210> SEQ ID NO 57
<211> LENGTH: 12
<212> TYPE: PRT
<213> ORGANISM: Powassan virus

<400> SEQUENCE: 57

Ala Leu Pro Trp Lys His Lys Asp Asn Gln Asp Trp
1               5                   10

<210> SEQ ID NO 58
<211> LENGTH: 12
<212> TYPE: PRT
<213> ORGANISM: Powassan virus

<400> SEQUENCE: 58

Leu Pro Trp Lys His Lys Asp Asn Gln Asp Trp Asn
1 5 10

<210> SEQ ID NO 59
<211> LENGTH: 12
<212> TYPE: PRT
<213> ORGANISM: Powassan virus

<400> SEQUENCE: 59

Pro Trp Lys His Lys Asp Asn Gln Asp Trp Asn Ser
1 5 10

<210> SEQ ID NO 60
<211> LENGTH: 16
<212> TYPE: PRT
<213> ORGANISM: Ehrlichia chaffeensis

<400> SEQUENCE: 60

Asn Ala Val Ser Gln Glu Thr Pro Ala Thr Gln Pro Gln Ser Arg Asp
1 5 10 15

<210> SEQ ID NO 61
<211> LENGTH: 19
<212> TYPE: PRT
<213> ORGANISM: Ehrlichia chaffeensis

<400> SEQUENCE: 61

Gln Glu Lys Thr Asn Pro Glu Val Leu Ile Lys Asp Leu Gln Asp Val
1 5 10 15

Ala Ser His

<210> SEQ ID NO 62
<211> LENGTH: 19
<212> TYPE: PRT
<213> ORGANISM: Ehrlichia chaffeensis

<400> SEQUENCE: 62

Gln Glu Glu Thr Asn Pro Glu Val Leu Ile Lys Asp Leu Gln Asp Val
1 5 10 15

Ala Ser His

<210> SEQ ID NO 63
<211> LENGTH: 16
<212> TYPE: PRT
<213> ORGANISM: Ehrlichia chaffeensis

<400> SEQUENCE: 63

Thr Asn Pro Glu Val Leu Ile Lys Asp Leu Gln Asp Val Ala Ser His
1 5 10 15

<210> SEQ ID NO 64
<211> LENGTH: 15
<212> TYPE: PRT
<213> ORGANISM: Ehrlichia chaffeensis

<400> SEQUENCE: 64

Lys Thr Asn Pro Glu Val Leu Ile Lys Asp Leu Gln Asp Val Ala
1 5 10 15

<210> SEQ ID NO 65
<211> LENGTH: 19
<212> TYPE: PRT
<213> ORGANISM: Ehrlichia chaffeensis

<400> SEQUENCE: 65

Ser Ala Tyr Val Tyr Cys Asp Lys Asp Gly Asn Glu Tyr Phe Asn Thr
1 5 10 15

Gln Ser Tyr

<210> SEQ ID NO 66
<211> LENGTH: 16
<212> TYPE: PRT
<213> ORGANISM: Ehrlichia chaffeensis

<400> SEQUENCE: 66

Leu Tyr Gly Leu Lys Gln Asp Trp Asn Gly Val Ser Ala Ser Ser His
1 5 10 15

<210> SEQ ID NO 67
<211> LENGTH: 19
<212> TYPE: PRT
<213> ORGANISM: Ehrlichia chaffeensis

<400> SEQUENCE: 67

Gly Val Phe Gly Leu Lys Gln Asp Trp Asp Gly Ser Ala Ile Pro His
1 5 10 15

Thr Gln Ser

<210> SEQ ID NO 68
<211> LENGTH: 16
<212> TYPE: PRT
<213> ORGANISM: Ehrlichia chaffeensis

<400> SEQUENCE: 68

His Val Tyr Thr Leu Lys Glu Ser Pro Lys Val Thr Ser Ala Val Ala
1 5 10 15

<210> SEQ ID NO 69
<211> LENGTH: 22
<212> TYPE: PRT
<213> ORGANISM: Ehrlichia chaffeensis

<400> SEQUENCE: 69

Tyr Asn Thr Thr Gln Leu Val Gly Leu Lys Lys Asp Ile Ser Val Ile
1 5 10 15

Gly Asn Ser Asn Ile Thr
20

<210> SEQ ID NO 70
<211> LENGTH: 19
<212> TYPE: PRT
<213> ORGANISM: Ehrlichia chaffeensis

<400> SEQUENCE: 70

Asp Thr Lys Gln Leu Val Ser Tyr Gly Lys Thr Pro Asn Ser Ile Asp
1 5 10 15

Leu Lys Thr

<210> SEQ ID NO 71
<211> LENGTH: 15
<212> TYPE: PRT
<213> ORGANISM: Ehrlichia chaffeensis

<400> SEQUENCE: 71

Asp Leu Gln Gln Ser Ser Asn Ser Asp Leu His Gly Ser Phe Ser 1 5 10 15

<210> SEQ ID NO 72
<211> LENGTH: 13
<212> TYPE: PRT
<213> ORGANISM: Borrelia burgdorferi

<400> SEQUENCE: 72

Val Gln Glu Gly Ala Gln Gln Glu Gly Ala Gln Gln Pro
1 5 10

<210> SEQ ID NO 73
<211> LENGTH: 15
<212> TYPE: PRT
<213> ORGANISM: Borrelia burgdorferi

<400> SEQUENCE: 73

Lys Ala Ile Leu Ile Thr Asp Ala Ala Lys Asp Lys Gly Ala Ala
1 5 10 15

<210> SEQ ID NO 74
<211> LENGTH: 17
<212> TYPE: PRT
<213> ORGANISM: Borrelia burgdorferi

<400> SEQUENCE: 74

Met Lys Lys Asp Asp Gln Ile Ala Ala Ala Ile Val Leu Arg Gly Met
1 5 10 15

Ala

<210> SEQ ID NO 75
<211> LENGTH: 14
<212> TYPE: PRT
<213> ORGANISM: Borrelia burgdorferi

<400> SEQUENCE: 75

Asn Ser Gly Lys Gly Gly Asp Ser Ala Ser Thr Asn Pro Ala
1 5 10

<210> SEQ ID NO 76
<211> LENGTH: 16
<212> TYPE: PRT
<213> ORGANISM: Borrelia burgdorferi

<400> SEQUENCE: 76

Ser Cys Asn Asn Ser Gly Lys Asp Gly Asn Thr Ser Ala Asn Ser Ala
1 5 10 15

<210> SEQ ID NO 77
<211> LENGTH: 15
<212> TYPE: PRT
<213> ORGANISM: Borrelia burgdorferi

<400> SEQUENCE: 77

Asn Ser Val Lys Glu Leu Thr Ser Pro Val Val Ala Glu Ser Pro
1 5 10 15

<210> SEQ ID NO 78
<211> LENGTH: 20
<212> TYPE: PRT
<213> ORGANISM: Anaplasma phagocytophilum

<400> SEQUENCE: 78

His Arg Val Val Gly Asp Gly Val Tyr Asp Asp Leu Pro Ala Gln Leu 1 5 10 15

Pro Thr Asn Asn
20

<210> SEQ ID NO 79
<211> LENGTH: 13
<212> TYPE: PRT
<213> ORGANISM: Anaplasma phagocytophilum

<400> SEQUENCE: 79

Phe Asp Trp Asn Thr Pro Asp Pro Asp Pro Arg Ile Gly
1 5 10

<210> SEQ ID NO 80
<211> LENGTH: 15
<212> TYPE: PRT
<213> ORGANISM: Anaplasma phagocytophilum

<400> SEQUENCE: 80

Trp Asn Thr Pro Asp Pro Arg Ile Gly Phe Lys Asp Asn Met Leu
1 5 10 15

<210> SEQ ID NO 81
<211> LENGTH: 20
<212> TYPE: PRT
<213> ORGANISM: Borrelia miyamotoi

<400> SEQUENCE: 81

Ile Ala Ala Gly Ile Ala Leu Arg Ala Met Ala Lys Asp Gly Lys Phe
1 5 10 15

Ile Val Lys Asp
20

<210> SEQ ID NO 82
<211> LENGTH: 13
<212> TYPE: PRT
<213> ORGANISM: Borrelia miyamotoi

<400> SEQUENCE: 82

Lys Lys Ile Lys Asp Ala Val Glu Phe Ala Ala Asn Val
1 5 10

<210> SEQ ID NO 83
<211> LENGTH: 13
<212> TYPE: PRT
<213> ORGANISM: Borrelia miyamotoi

<400> SEQUENCE: 83

Lys Lys Ile Lys Asp Ala Val Glu Phe Ala Ala Ser Val
1 5 10

<210> SEQ ID NO 84
<211> LENGTH: 20
<212> TYPE: PRT
<213> ORGANISM: Borrelia miyamotoi

<400> SEQUENCE: 84

Ile Gly Cys Asn Asn Gly Gly Gly Glu Asp Pro Gln Lys Val Phe Leu
1 5 10 15

Thr Ser Ile Ala
20

<210> SEQ ID NO 85

<211> LENGTH: 18
<212> TYPE: PRT
<213> ORGANISM: Borrelia miyamotoi

<400> SEQUENCE: 85

Lys Asn Ile Glu Glu Ala Lys Asp Ala Ala Ser Ile Ala Ala Ala Lys
1 5 10 15

Gln Thr

<210> SEQ ID NO 86
<211> LENGTH: 19
<212> TYPE: PRT
<213> ORGANISM: Borrelia miyamotoi

<400> SEQUENCE: 86

Ala Lys Glu Glu Asn Ile Ala Lys Ala Ser Ala Ser Ile Gly Ala Val
1 5 10 15

Ser Gly Ala

<210> SEQ ID NO 87
<211> LENGTH: 16
<212> TYPE: PRT
<213> ORGANISM: Borrelia miyamotoi

<400> SEQUENCE: 87

Gly Ile Glu Gln Ala Lys Asn Ala Ala Glu Ile Ala Ala Ala Lys Asn
1 5 10 15

<210> SEQ ID NO 88
<211> LENGTH: 15
<212> TYPE: PRT
<213> ORGANISM: Borrelia miyamotoi

<400> SEQUENCE: 88

Thr Ser Glu Ala Lys Ile Glu Thr Ala Lys Asp Ala Ala Ser Ile
1 5 10 15

<210> SEQ ID NO 89
<211> LENGTH: 14
<212> TYPE: PRT
<213> ORGANISM: Borrelia miyamotoi

<400> SEQUENCE: 89

Ile Glu Glu Ala Lys Asp Ala Ala Ser Ile Ala Ala Ala Lys
1 5 10

<210> SEQ ID NO 90
<211> LENGTH: 16
<212> TYPE: PRT
<213> ORGANISM: Powassan virus

<400> SEQUENCE: 90

Glu Asp Leu Ala Leu Pro Trp Lys His Lys Asp Asn Gln Asp Trp Asn
1 5 10 15

<210> SEQ ID NO 91
<211> LENGTH: 16
<212> TYPE: PRT
<213> ORGANISM: Babesia microti

<400> SEQUENCE: 91

Gly Thr Gly Trp Pro Ser Glu Ala Gly Gly Pro Ser Glu Ala Gly Gly
1 5 10 15

<210> SEQ ID NO 92
<211> LENGTH: 13
<212> TYPE: PRT
<213> ORGANISM: Babesia microti

<400> SEQUENCE: 92

Asn Lys Ser Gly Asn Ala Gly Ile Lys Ser Tyr Asp Thr
1 5 10

<210> SEQ ID NO 93
<211> LENGTH: 18
<212> TYPE: PRT
<213> ORGANISM: Babesia microti

<400> SEQUENCE: 93

Glu Gly Glu Ser His Lys Glu Tyr Val Ala Glu Lys Thr Lys Glu Ile
1 5 10 15

Asp Glu

<210> SEQ ID NO 94
<211> LENGTH: 17
<212> TYPE: PRT
<213> ORGANISM: Babesia microti

<400> SEQUENCE: 94

Glu Gly His Gly Lys Pro Asn Thr Asn Lys Ser Glu Lys Ala Glu Arg
1 5 10 15

Lys

<210> SEQ ID NO 95
<211> LENGTH: 15
<212> TYPE: PRT
<213> ORGANISM: Anaplasma phagocytophilum

<400> SEQUENCE: 95

Arg Leu Val Asp Asp Thr Ser Pro Ala Gly Arg Thr Lys Asp Thr
1 5 10 15

<210> SEQ ID NO 96
<211> LENGTH: 14
<212> TYPE: PRT
<213> ORGANISM: Borrelia miyamotoi

<400> SEQUENCE: 96

Ser Ala Ala Gln Asn Val Lys Thr Ala Glu Glu Leu Gly Met
1 5 10

<210> SEQ ID NO 97
<211> LENGTH: 15
<212> TYPE: PRT
<213> ORGANISM: Ehrlichia chaffeensis

<400> SEQUENCE: 97

Asn Thr Ala Gln Leu Val Gly Leu Lys Lys Asp Ile Ser Ile Thr
1 5 10 15

<210> SEQ ID NO 98
<211> LENGTH: 13
<212> TYPE: PRT
<213> ORGANISM: Powassan virus

<400> SEQUENCE: 98

Leu Ala Leu Pro Trp Lys His Lys Asp Asn Gln Asp Trp 1 5 10

<210> SEQ ID NO 99
<211> LENGTH: 14
<212> TYPE: PRT
<213> ORGANISM: Babesia microti

<400> SEQUENCE: 99

His Gln Glu Gln Asn Asn Ala Asn Asp Ser Ser Asn Pro Thr
1 5 10

<210> SEQ ID NO 100
<211> LENGTH: 15
<212> TYPE: PRT
<213> ORGANISM: Babesia microti

<400> SEQUENCE: 100

Asn Lys Ser Gly Lys Ala Gly Ile Lys Ser His Asn Thr Gln Thr
1 5 10 15

<210> SEQ ID NO 101
<211> LENGTH: 14
<212> TYPE: PRT
<213> ORGANISM: Ehrlichia chaffeensis

<400> SEQUENCE: 101

Thr Asn Pro Glu Val Leu Ile Lys Asp Leu Gln Asp Val Ala
1 5 10

<210> SEQ ID NO 102
<211> LENGTH: 14
<212> TYPE: PRT
<213> ORGANISM: Ehrlichia chaffeensis

<400> SEQUENCE: 102

Tyr Val Tyr Cys Asp Lys Asp Gly Asn Glu Tyr Phe Asn Thr
1 5 10

<210> SEQ ID NO 103
<211> LENGTH: 12
<212> TYPE: PRT
<213> ORGANISM: Ehrlichia chaffeensis

<400> SEQUENCE: 103

Leu Tyr Gly Leu Lys Gln Asp Trp Asn Gly Val Ser
1 5 10

<210> SEQ ID NO 104
<211> LENGTH: 13
<212> TYPE: PRT
<213> ORGANISM: Ehrlichia chaffeensis

<400> SEQUENCE: 104

Gln Gln Ser Ser Asn Ser Asp Leu His Gly Ser Phe Ser
1 5 10

<210> SEQ ID NO 105
<211> LENGTH: 12
<212> TYPE: PRT
<213> ORGANISM: Borrelia burgdorferi

<400> SEQUENCE: 105

Val Gly Met Thr Phe Arg Ala Gln Glu Gly Ala Phe
1 5 10

```
<210> SEQ ID NO 106
<211> LENGTH: 13
<212> TYPE: PRT
<213> ORGANISM: Borrelia burgdorferi

<400> SEQUENCE: 106

Lys Ile Thr Lys Leu Thr Pro Glu Glu Leu Glu Asn Leu
1               5                   10


<210> SEQ ID NO 107
<211> LENGTH: 13
<212> TYPE: PRT
<213> ORGANISM: Anaplasma phagocytophilum

<400> SEQUENCE: 107

Thr Ser Gly Lys Asp Ile Val Gln Phe Ala Lys Ala Val
1               5                   10


<210> SEQ ID NO 108
<211> LENGTH: 11
<212> TYPE: PRT
<213> ORGANISM: Borrelia miyamotoi

<400> SEQUENCE: 108

Lys Lys Ile Lys Asp Ala Val Glu Phe Ala Ala
1               5                   10


<210> SEQ ID NO 109
<211> LENGTH: 12
<212> TYPE: PRT
<213> ORGANISM: Borrelia miyamotoi

<400> SEQUENCE: 109

Ile Glu Glu Ala Lys Asp Ala Ala Ser Ile Ala Ala
1               5                   10


<210> SEQ ID NO 110
<211> LENGTH: 14
<212> TYPE: PRT
<213> ORGANISM: Borrelia miyamotoi

<400> SEQUENCE: 110

Cys Asn Asn Gly Gly Gly Glu Asp Pro Gln Lys Val Phe Leu
1               5                   10
```